US008652804B2

(12) United States Patent  
Dietrich et al.

(10) Patent No.: US 8,652,804 B2
(45) Date of Patent: Feb. 18, 2014

(54) TRANSCRIPTION FACTOR-BASED BIOSENSORS FOR DETECTING DICARBOXYLIC ACIDS

(75) Inventors: Jeffrey Dietrich, San Francisco, CA (US); Jay Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/399,744

(22) Filed: Feb. 17, 2012

(65) Prior Publication Data
US 2012/0219971 A1 Aug. 30, 2012

Related U.S. Application Data

(60) Provisional application No. 61/444,302, filed on Feb. 18, 2011.

(51) Int. Cl.
*C12P 1/00* (2006.01)

(52) U.S. Cl.
USPC ............ 435/41; 506/10; 506/14; 506/7

(58) Field of Classification Search
None
See application file for complete search history.

(56) References Cited

U.S. PATENT DOCUMENTS

| | | | | |
|---|---|---|---|---|
| 5,962,624 | A * | 10/1999 | Vonderhagen et al. | 528/274 |
| 6,162,627 | A * | 12/2000 | Inouye et al. | 435/194 |
| 6,316,220 | B1 * | 11/2001 | Christensen | 435/69.1 |
| 2005/0176118 | A1 * | 8/2005 | Oakeshott et al. | 435/128 |
| 2007/0122812 | A1 * | 5/2007 | Hoff | 435/6 |
| 2008/0070231 | A1 * | 3/2008 | Franciskovich et al. | 435/5 |
| 2008/0103060 | A1 * | 5/2008 | Gill et al. | 506/10 |
| 2009/0139134 | A1 * | 6/2009 | Yoshikuni et al. | 44/307 |
| 2012/0238470 | A1 * | 9/2012 | Lee et al. | 506/11 |
| 2012/0329111 | A1 * | 12/2012 | Burgard et al. | 435/148 |

OTHER PUBLICATIONS

Uyama, H et al, J. Polym. Sci, A: Polym Chem. vol. 37, pp. 2737-2745, 1999, Lipase-catalyzed Polycondensation of Dicarboxylic Acid-Divinyl Esters and Glycols to Aliphatic Polyesters.*
Namekawa, Shuhei et al, Biomacromolecules 2000, vol. 1, pp. 335-338, Enzymatic Synthesis of POlyesters from lactones, Dicarboxylic acid divinyl esters and glycols through combinaiton of ring-opening polymerization and polycondensation.*
Okada, Mashiko et al, Journal of Applied Polymer Science, vol. 77, pp. 338-346, 2000 Biodegradable Polymers Based on Renewable Resources. IV. Enzymatic Degradation of Polyesters Composed of 1,4:3.6 Dianhydro-D-glucitol and Aliphatic Dicarboxylic Acid moieties.*
Guo, Zhu et al, Molecular Microbiology, 1999, vol. 32(2), pp. 253-263, PcaR-mediated activation and repression of pca genes from Pseudomonas putida are propagated by its binding to both the -35 and the -10 promoter elements.*

* cited by examiner

*Primary Examiner* — Albert Navarro
*Assistant Examiner* — Ginny Portner
(74) *Attorney, Agent, or Firm* — Kilpatrick Townsend & Stockton LLP

(57) ABSTRACT

The invention provides methods and compositions for detecting dicarboxylic acids using a transcription factor biosensor.

6 Claims, 8 Drawing Sheets

Figure 1

```
gi|227820367   M----------------------R----------ETDFVSGFARGLEVIEAF  20
gi|306840718   M----------------------R----------ETDFVGCFAKGLRVIEAF  20
gi|312959480   MNDQL-----------RNSFASAAPPI-VASP-AKRIQAPTGDPDFMTSLARGLAVVQAF  47
gi|66047241    MNDEL-----------RKSFASLAPPI-VASP-AKRIQALTGDPDFMTSLARGLAVIHAF  47
PcaR           MSDETFANESANPESARFAAFALAPPI-VASP-AKRIQAPTGDPDFMTSLARGLAVIQAF  58
gi|15595353    MS-ELPEHP---------ATLAPPT-VLSP-AKPIEAPTGDPNFMTSLARGLAVIHAF   46
gi|116696481   MDVLRPLGLGHAQ---------ADTVRVAKPQADLLASFAGDPNPMLSLARGLTVLEAF  50
gi|283785372   MEK-HPDDRLNNE----------ADP--------PKGDPNFMASLARGLEVIQAF     36
gi|218548989   MEK-HPDDRLNSD----------ADP--------FKGDPNFMASLARGLDVIQAF     36
gi|206580726   MDK-HPDDLLTGD----------GDP--------PKGDPNFMASLARGLEVIQAF     36
gi|296118524   MVS--------------------PS---------SDFVQSFARGLMVIRSF         22 gi|227820367   GEAQPRLSIAEASKITGLDRATVRRSLLTLSELGYADY-DGKFPTLTPRILRLGHAYLSA  79
gi|306840718   GEDRPPLSIADVSKITGLDPATARPCLLTLAELGYABY-DGKFPMLRPPILRLGHRYLSG  79
gi|312959480   QERKRHLTIAQISHRTEIPRAAVPRCLHTLIKLGYATT-DGRTYSLLPKVLTLGHAILSS 106
gi|66047241    QERKRHLTIAQISHRTEIPRAAVRRCLHTLIPLGYATT-DGRTYSLLPEVLTLGHAYLSS 106
PcaR           QERKRHLTIAQISHRTEIPRAAVPRCLHTLIKLGYATT-DGRTYSLLPKVLTLGHAYLSS 117
gi|15595353    QERKRHLTIAQISHRTEIPRAAVRRCLHTLMQLGYATT-DGRTYSLLPEVLTLGHAYLSS 105
gi|116696481   SERKPPLTISQVAQRTQLSPASVERCLYTLEQLGYVSQQDG--QFALRPRVLRLGHAYFSS 109
gi|283785372   TPQRVLSISQISQKTGIPRAAVERCLYTLSKLGFVYAQDGKNFELRPKILALGHAYLAS  96
gi|218548989   TPQKRMMSISQISQKTGIPPAAVRRCLYTLGKIGFVYAQDGKNFELRPPILALGHAYLAS  96
gi|206580726   TPQRPLLSISQISQKTGIPRAAVPRCLYTLSKLGFVYAEDGKNFQLRPKILALGHAWLAS  96
gi|296118524   DATAPSQTLSQVAABTGLSPAAARPFLHTLVEEGYAVN-NDGQPFSLTPPVMELGYSYLSA  81 gi|227820367   TPLPAIVQPYLDQLSEKAGQSASASVLDGTEVVYVARAS-QPRVMSINLMPGSRLPAYCA 138
gi|306840718   TPLPTIIQPHLDRLSQSVGESASASVLDGAEIVYIARAS-QMRVISINLMAGSRLPAYCA 138
gi|312959480   TPLAVSAQPYLDRMSEQLHEACNMATLEGDDILYIARSATTQRLISVDLSVGGRLPAYCT 166
gi|66047241    TPLATSSQPYLDRMSDQLHEACNMATLEGDDILYIARSATTQRLISVDLSVGGRLPAYCT 166
PcaR           TPLAISAQPYLDRISDQLHEAANMATLEGDDILYIARSATVERLISVDLSVGGRLPAYCT 177
gi|15595353    TPLAITAQPILDPLSEQLHEACSMATLEGDDVLYIAPSATPQRLISVDLNVGSPLPAYCT 165
gi|116696481   TSLVSLAQPILDNLSARIHETCTLAILDGTDILYLVKSE--VQPVLNYSLGMGSRLPAYCT 168
gi|283785372   TPLARATQPVLKHLSEMLNESCSIATLDGDDILYIARAS-SSKIMTIDLDIGSRLPAWST 155
gi|218548989   TPLAPAAQPVLKHLSEMLNESCSIATLDGDDILYIARAS-SSPIMTIDLDIGSRLPAWAT 155
gi|206580726   TPLARSQPVLKHLSEMLNESCSIATLDGDDILYIARAS-SSKIMTIDLDIGSRLPAWAT 155
gi|296118524   LNLFALAQPFELEGLSAQVGESCSMSVLDGTDIHYVSRVA-VREIMTVNITIGTRFPAHST 140 gi|227820367   SMGRVLLAALPEAEAREILGRTELKA-NTPRTKTDLEELMAEFPKVRELGYAVIDQELEL 197
gi|306840718   SMGRVLLAWLDESEARTILEQTELQA-RTPFTQTDLEKLMEELKRISAQGFAVNDQELEL 197
gi|312959480   SMGRILLAALDDASLQDYLDHADLQT--KTSRTITTPEALFECLQQVRQQGWCIVDQELEQ 225
gi|66047241    SMGRILLAALDDVSLHEYLDEVDLQP-KTSPTIRTPEALLECLQLVRQQGWCIVDQELEQ 225
PcaR           SMGRILLAAMDDTSLREYLDRADLFA-KTSRTLNDAESLFACIQQVRAQGWCVVDQELEQ 236
gi|15595353    SMGRILLAALDDDALHAYPGGVEMQA-KTSPTLYTPETLLPCLVEIRPQGWCIVDQELEV 224
gi|116696481   SNGRLLLAKQPATVLDGFFEHAELRP-PTLQTKVSRQELEACFERAPEVDYVIVDRELEP 227
gi|283785372   SMGRVLSHLSEDELNDMLGRITMIR-YTSQTVDSVAALRAELKRVRQQGYALNDQELEM 214
gi|218548989   SMGRPVLLSHLPEENLNDLLGPVTMIR-YTSQTVDSVSALEELKKVQQQGYALNDQELEM 214
gi|206580726   SMGRVLLSKQFEEKLNDMLARVTMIR-YTPQTVDSVAKLRTELKRVHQQGYALNDQELEM 214
gi|296118524   SMGRVILSGMPDADIRSFLDSVPLEHGLTPPSLTDKEQLFAEIIAVRNQGWSLVDQELEL 200 gi|227820367   GLCSIAVPLMNAKGQVVAALNIGAPAAHVAKSELAEKYLPLLFETQAALRPLVQ---- 251
gi|306840718   GLRSIAVFVFNHPGAVVAALNIGAFVAHVEVSDLVGRILPEMLEIQSELRSMLP---- 251
gi|312959480   GLRSIAVPVYDASGQVLAALNVSTHAGRVSRSELEQRFLPSMLSASRELSTQLFA--- 280
gi|66047241    GLRSIAVPVYDASGQVLAALNVTSAGRVARSELEQRFLPIMLDASRDLSTQLFT--- 280
PcaR           GLRSIAVPIYDASGQVLAALNVSTHVGRVTRSELEQRFLPILLAASRDLCHQLFG--- 291
gi|15595353    GLRSIAVPVRDSAGRVLAALNVGTHACRVSPAELESKFLPLLLEASRELSARLFT--- 279
gi|116696481   GLPAMAVPVRSASGIVLAGLSVSVPAARVSETEMISPLLFPIREAAAAIGRLISS--- 282
gi|283785372   GLRSIAVPLANAQGQVQAALNVGVHAGQVTAEELRTKVLPELQKAAQELSLLLD---- 268
gi|218548989   GLRSIAVPLSNTPGQVLAALNVGVHAGQVBADELLSPVLPELQFAAQQELSLLLD---- 268
gi|206580726   GLRSIAVPLFNAQGQVQAALNVGVHAGQMSAKEMIDKVLPELQKAAARELTLLLR---- 268
gi|296118524   GLRSLAAPIFDADGEIVAAINISTQSAVSSVHELTSNYLPVLLATADEISRDLRMAST 258
```

TRANSCRIPTION FACTOR-BASED BIOSENSORS FOR DETECTING DICARBOXYLIC ACIDS

CROSS-REFERENCE TO RELATED APPLICATIONS

The application claims benefit of U.S. provisional application No. 61/444,302, filed Feb. 18, 2011, which application is herein incorporated by reference for all purposes.

STATEMENT AS TO RIGHTS TO INVENTIONS MADE UNDER FEDERALLY SPONSORED RESEARCH AND DEVELOPMENT

The invention described and claimed herein was made in part utilizing funds supplied by the U.S. Department of Energy under Contract No. DE-AC02-05CH11231. The government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-91-1.TXT, created on Mar. 30, 2012, 69,632 bytes, machine format IBM-PC, MS-Windows operating system, is hereby incorporated by reference in its entirety for all purposes.

BACKGROUND OF THE INVENTION

Dicarboxylic acids (diacids) are important compounds that are used in the manufacture of commercial polymers (e.g. polyesters, polyurethanes). Recently, methods and compositions for generating diacids by engineering microorganisms to produce diacids have been described (see, e.g., WO2009/121066, incorporated by reference).

The ability to sensitively and rapidly quantify dicarboxylic acid titers from production strains of microorganisms is difficult to accomplish to date. The identification of improved production strains requires variant libraries ranging in size from $10^2$ to $10^9$ to be constructed and screened in an experiment; in general, the larger the library size screened the higher the probability of identifying improved production variants. Screening by liquid chromatography-mass spectrometry, which is the gold-standard in dicarboxylic acid quantification, suffers from low-throughputs and only $10^2$-$10^3$ samples can be reasonably analyzed per experiment. Intramolecular excimer-forming fluorescence derivatization was recently demonstrated for detection of dicarboxylic acids in urine samples; the method offers improved throughputs ($\sim 10^4$-$10^5$ variants per experiment), but requires extraction with organic solvents, multiple liquid handling steps, and derivatization of the diacid substrate for detection. The above factors impart significant costs that prohibit large-scale implementation of this screening setup. There thus remains need for a low-cost, high-throughput, accurate, and sensitive dicarboxylic acid screening assay. This invention addressed this need.

BRIEF SUMMARY OF THE INVENTION

The present invention is based, in part, on the discovery that a biosensor-based system can be used for the accurate detection of exogenous dicarboxylic acids in liquid or solid media and in vivo detection of endogenously produced diacids within a host. Microorganisms are highly adept at sensing and responding to small-molecules in their environment. For example, transcription factors that bind dicarboxylic acids can modulate expression of one or more reporter genes downstream of the transcription factor's cognate promoter. By monitoring the expression of the reporter genes dicarboxylic acid concentration can be readily measured.

Thus, in some embodiments, the invention provides a recombinant host cell comprising a transcription factor biosensor comprising: a transcription factor that can bind to and activate a promoter; a protein moiety that binds a dicarboxylic acid; and a promoter that is activated by the transcription factor, where the promoter is operably linked to a nucleic acid sequence that encodes a heterologous reporter gene. In some embodiments, the recombinant host cell comprises a heterologous nucleic acid encoding the transcription factor and/or a heterologous nucleic acid that encodes the moiety that binds the dicarboxylic acid, and/or a nucleic acid comprising a heterologous promoter operably linked to the reporter gene. In some embodiments, an endogenous transcription factor gene corresponding to the transcription factor sensor gene and/or an endogenous promoter sequence that the transcription factor binds to are inactivated in the recombinant host cell. The dicarboxylic acid to which the dicarboxylic binding moiety binds may be a C4, C5, C6, or C7 dicarboxylic acid. In some embodiments, the dicarboxylic acid is a C8, C9, C10, C11, C12, C13, or C14 dicarboxylic acid. In some embodiments, the dicarboxylic acid has a backbone comprising an even number of carbon atoms. In other embodiments, the dicarboxylic acid has a backbone comprising an odd number of carbon atoms.

In some embodiments of the invention, the transcription factor itself comprises the protein moiety that binds the dicarboxylic acid, e.g., the transcription factor may be a PcaR transcription factor. In some embodiments, the promoter that is operably linked to a reporter gene to which a PcaR polypeptides binds is a PcaR promoter or a PcaIJ promoter. In some embodiments, the host cell further comprises a nucleic acid sequence encoding a dicarboxylic acid transporter to transport, e.g., uptake, exogenous dicarboxylic acid.

In some embodiments of a dicarboxylic acid biosensor system of the invention, the polypeptide moiety that binds the dicarboxylic acid is membrane associated sensory protein, e.g., a histidine kinase sensory protein, that is capable of binding to and detecting exogenous dicarboxylic acid. In some embodiments, the transcription factor is DcuR and the protein moiety that binds the dicarboxylic acid is a DcuS histidine kinase. In some embodiments where the transcription factor/sensor is a DcuR-DcuS, the promoter operably linked to a reporter gene may be, e.g., a DcuB promoter, a DctA promoter or a FrdA promoter. In some embodiments, the transcription factor is a DctD transcription factor and the moiety that binds the dicarboxylic acid is a DctB histidine kinase and the promoter linked to the reporter gene is, e.g., a DctA promoter. In some embodiments, e.g., where a DctD-DctB transcription factor/sensor is employed, a recombinant host further comprises a nucleic acid encoding a heterologous σ 54-RNA polymerase.

A recombinant host cell comprising a dicarboxylic acid biosensor system of the invention may be any kind of prokaryotic cell, e.g., in some embodiments, the recombinant host cell is *Escherichia coli*.

In a further aspect, the invention provides a method of detecting a dicarboxylic acid, the method comprising providing a recombinant host cell that comprises a dicarboxylic acid biosensor described herein and detecting expression of the reporter gene. In some embodiments, the method detects the presence of dicarboxylic acid that is produced by the host cell.

In some embodiments, the host cell is contacted with a mixture, e.g., cell culture media, that is being analyzed for the presence of one or more dicarboxylic acids.

The invention further provides a mixture capable of transcribing RNA, the mixture comprising a transcription factor biosensor comprising components as described herein: a transcription factor that can bind to and activate a promoter; a protein moiety that binds a dicarboxylic acid; and the promoter that is activated by the transcription factor operably linked to a nucleic acid sequence that encodes a heterologous reporter gene. The protein moiety that binds the dicarboxylic acid may be part of the transcription factor, e.g., a PcaR transcription factor; or present on a separate polypeptide, e.g., a DcuS polypeptide in a DcuS-DcuR system; or a DctD-DctB system. In some embodiments, the mixture further comprises at least one dicarboxylic acid.

BRIEF DESCRIPTION OF THE DRAWINGS

FIG. 1 provides an alignment of PcaR transcription factor amino acid sequences. A multiple sequence alignment of PcaR with ten representative protein sequences from the NCBI database (SEQ ID NOS:18-27), redundant sequences from different strains of the same species were excluded from the alignment. Each of the sequences is named by its gene ID; the sequence designated as "PcaR" is the reference sequence SEQ ID NO:6. SEQ ID NO:6 exhibits between 49% and 88% identity to the sequences shown in this alignment.

DETAILED DESCRIPTION OF THE INVENTION

I. Definitions

Figure 2:
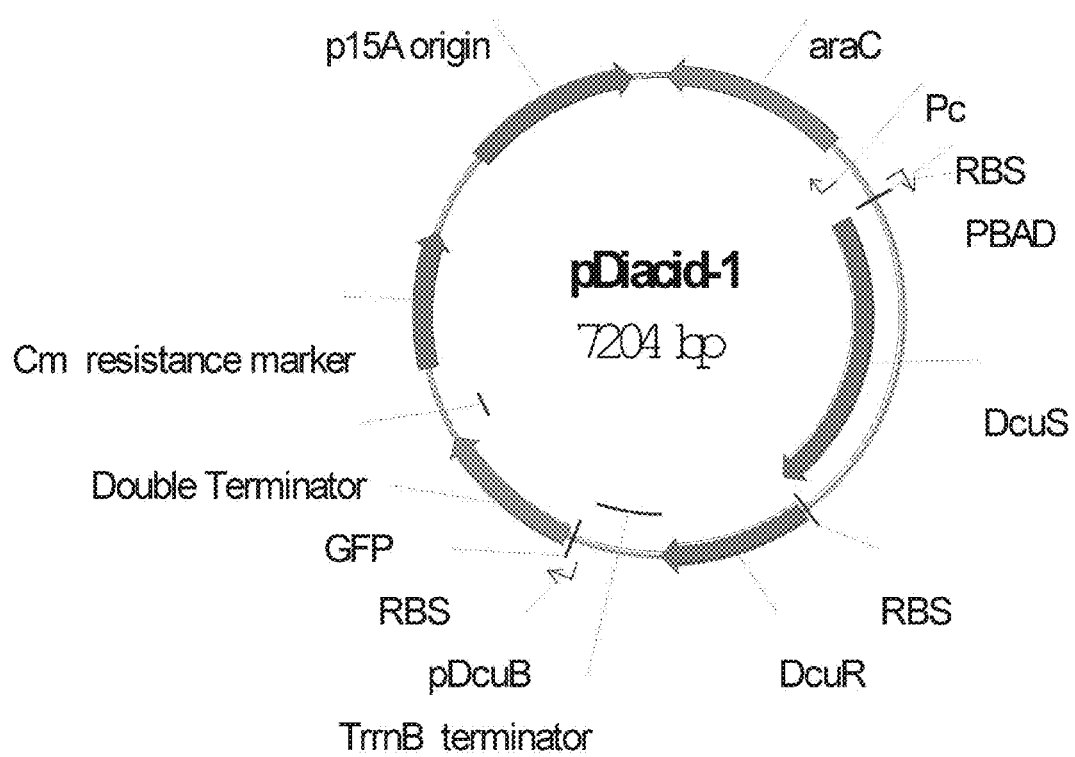
FIG. 2 provides a map of an illustrative plasmid of the invention, which encodes a dicarboxylic acid biosensor of the invention, that comprising nucleic acid sequences encoding DcuR and DcuS and a green fluorescent protein operably linked to a DcuB promoter.
Figure 3:
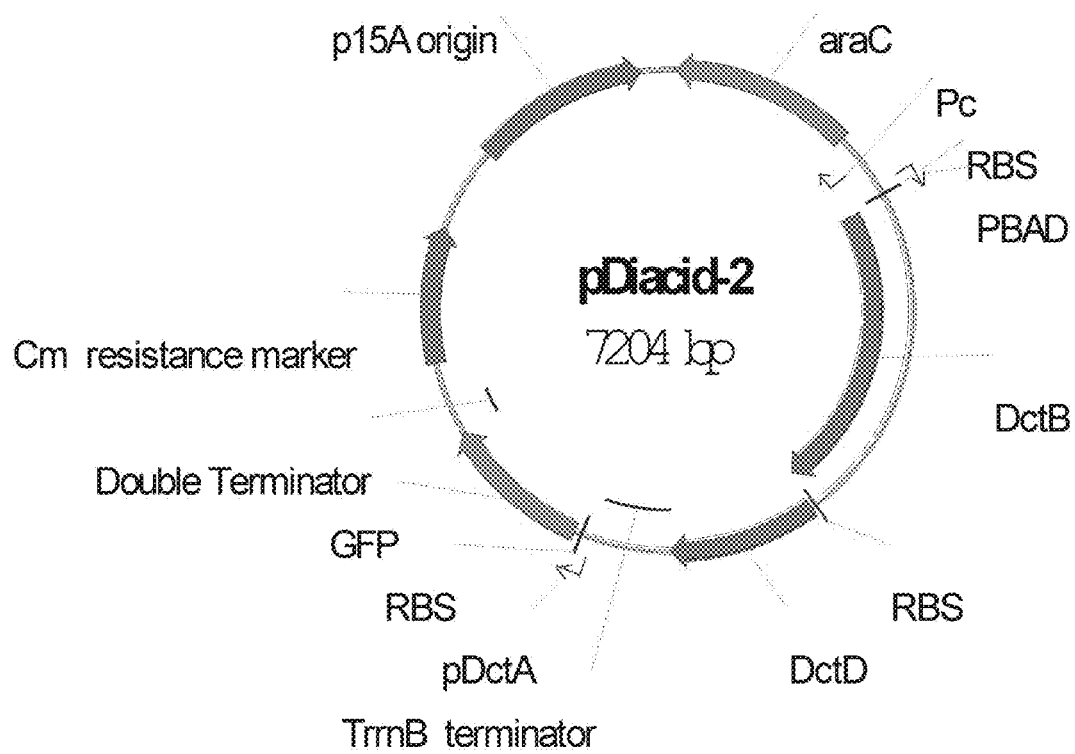
FIG. 3 provides a map of an illustrative plasmid of the invention, which encodes a dicarboxylic acid biosensor of the invention, where the plasmid is analogous to the plasmid shown in FIG. 2 in which the *Sinorhizobium meliloti* genes encoding for DctB and DctD replace the DcuR and DcuS genes; and a DctA promoter replaces the DcuB promoter.

The term "transcription factor biosensor" as used herein refers to a system to detect a dicarboxylic acid by activating expression of a reporter gene where reporter gene expression is mediated by a transcription factor that is capable of binding to a promoter and activating transcription upon binding of a dicarboxylic acid to a sensory protein that induces a change in transcription factor conformation from an inactive to an active form, or upon binding of a dicarboxylic acid to the transcription factor itself. For example, in an embodiment employing a sensory protein, a dicarboxylic acid may bind to a transmembrane receptor (e.g., DcuS) that upon binding the dicarboxylic acid, phosphorylates a transcription factor (e.g., DcuR); phosphorylated DcuR is active and promotes transcription from its cognate promoter (e.g. $P_{DcuB}$). A "transcription factor biosensor" of the invention thus comprises a transcription factor that has a DNA binding domain and an activation domain such that the transcription factor is capable of binding to and activating a promoter; a protein moiety that binds a dicarboxylic acid; and a reporter gene expressed from a coding sequence operably linked to a promoter that is activated by the transcription factor. The protein moiety that binds to the dicarboxylic acid may be part of the transcription factor or may be present in a different protein, e.g., a transmembrane protein in which the dicarboxylic acid binding moiety can bind to exogenous dicarboxylic acids.

As used herein, the term "transcription factor that is activated by dicarboxylic acid" refers to a transcription factor that binds to a dicarboxylic acid or that responds to a signal generated from a protein that binds the dicarboxylic acid.

The term "downstream target," when used in the context of a downstream target of a transcription factor that activates a promoter refers to a gene or protein whose expression is directly or indirectly regulated by the transcription factor.

The term "activation of a promoter" refers to inducing expression of a gene that is operably linked to the promoter. In the context of this invention, a promoter is activated either when a transcription factor that is part of a transcription factor biosensor system of the invention binds to the promoter such that gene expression can be initiated, or when a transcription factor that is part of a transcription factor biosensor system of the invention binds to the target ligand and the promoter is derepressed. Activation can be determined relative to the level of gene expression when the transcription factor is not bound to the target ligand. Alternatively, activation is determined relative to the level of gene expression when the target ligand is not present or is present at some designated level or concentration.

In the context of the current invention, a host cell "capable of expressing" a reporter gene when a transcription factor biosensor of the invention binds to a promoter coupled to the reporter gene in response to the presence of a dicarboxylic acid in the environment, refers to a host cell that has an RNA polymerase that is responsive to the promoter and the transcription factor such that transcription of the reporter gene can be initiated. In the current context, "activation" of an RNA polymerase by a transcription factor refers to activation by interaction of the transcription factor with the polymerase, as well as to activation that is mediated by the promoter, i.e., where binding of the transcription factor to the promoter enables the RNA polymerase to better bind to the promoter and transcribe the gene.

A "mixture capable of transcribing RNA" in the context of this invention refers to a mixture that has all of the necessary components for transcription of a reporter gene, including but not limited to, a polymerase that is capable of being activated by the transcription factor upon binding of the transcription factor to a promoter, and any necessary cofactors and nucleotide triphosphates.

The terms "polynucleotide" and "nucleic acid" are used interchangeably and refer to a single or double-stranded polymer of deoxyribonucleotide or ribonucleotide bases. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" refers to the order of the bases in a polynucleotide or nucleic acid and includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a DNA/RNA hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of two nucleic acids or polypeptides, refers to a sequence that has at least 60% sequence identity with a reference sequence. Percent identity can be any integer from 60% to 100%. Some embodiments include at least: 60%, 65%, 70%, 75%, 80%, 85%, 90%, 91%, 92%, 93%, 94%, 95%, 96%, 97%, 98%, or 99% identity, over a region of at least 25 or 50 contiguous residues, typically at least 100, 200, 300, 400 or more contiguous residues, or over the full length, to a reference sequence compared using the programs described herein; preferably BLAST using standard parameters, as described below. In some embodiments, the percent identity is determined over the entire length of the reference sequence. For example, a polypeptide that is part of a transcription factor biosensor of the invention may have an amino acid sequence that is at least 60%, 65%, 70%, 75%, 80%, 85%, 90%, 91%, 92%, 93%, 94%, 95%, 96%, 97%, 98%, or 99% identical to a reference sequence of SEQ ID NO:1, SEQ ID NO:2, SEQ ID NO:6, SEQ ID NO:9 or SEQ ID NO:10 across the full-length of the reference sequence.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Alternatively, sequences may be manually aligned for comparison.

A "comparison window," as used herein, includes reference to a segment of any one of a number of contiguous positions, typically from about 20 to about 600 contiguous positions, usually about 50 to about 200 contiguous positions, or about 100 to about 150 contiguous positions, in which a sequence may be compared to a reference sequence of the same number of contiguous positions after the two sequences are optimally aligned. In some embodiments, comparison are over the length of the two sequences being compared. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad.*

Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups provides examples of conservative substitutions. Each group contains amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

The term "promoter," as used herein, refers to a polynucleotide sequence capable of driving transcription of a DNA sequence, which may be referred to herein as a "coding sequence", in a cell. The promoter comprises cis-acting regions that typically interact with proteins or other biomolecules to carry out (turn on/off, regulate, modulate, etc.) gene transcription. Promoters are located 5' to the transcribed gene, and as used herein, include the sequence 5' from the translation start codon. By convention, the promoter sequence is usually provided as the sequence on the coding strand of the gene it controls. A "gene" may thus typically include at least a promoter and a coding sequence.

A polynucleotide is "heterologous" to an organism or a second polynucleotide sequence if it originates from a foreign species, or, if from the same species, is modified from its original (native or naturally occurring) form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA sequence if it stimulates or modulates the transcription of the DNA sequence in an appropriate host cell or other expression system. In typical embodiments of the invention, promoter transcriptional regulatory sequences in the context of this invention, that are operably linked to a transcribed sequence are physically contiguous to the transcribed sequence, i.e., they are cis-acting.

The term "expression cassette" refers to a nucleic acid construct that, when introduced into a host cell, results in transcription and/or translation of an RNA or polypeptide, respectively. Constructs that are not or cannot be translated, e.g., particular promoter sequences that may be contained with an expression cassette, are expressly included by this definition.

The singular forms "a", "and", and "the" include plural referents unless the context clearly dictates otherwise. Thus, for example, reference to "a carboxylic acid" includes a plurality of such carboxylic acids, and so forth.

II. Introduction

The present invention is based, in part, on the discovery that a transcription-based biosensor system can be used for the accurate detection of exogenous dicarboxylic acids in liquid or solid media and in vivo detection of endogenously produced diacids within a host. Thus, the invention provides methods and compositions for identifying microorganisms that produce a dicarboxylic acid and/or produce the dicarboxylic acid at a desired level. In the current invention, a dicarboxylic acid binds to a protein moiety that is either present on a transcription factor itself or is part of a second protein that transduces a signal to the transcription factor. Binding of the dicarboxylic acid to the dicarboxylic acid binding moiety results in either binding of the transcription factor to the promoter that is activated by the transcription factor, or in some embodiments, results in derepression of the promoter by the dicarboxylic acid-bound transcription factor.

In some embodiments, the system is an in vitro system wherein all of the necessary components for transcription of the reporter gene, including but not limited to a polymerase that is capable of being activated by the transcription factor upon binding of the transcription factor to a promoter, and any necessary cofactors and nucleotide triphosphates, are present in the system. Accordingly, in some embodiments, the invention provides a mixture comprising a transcription factor biosensor of the invention, a promoter operably linked to a reporter gene where the promoter is a promoter that binds the transcription factor that is activated by the presence of a dicarboxylic acid, a polymerase, additional reagents, and in some embodiments, a dicarboxylic acid.

In some embodiments, the system is an in vivo system wherein all of the necessary components for transcription of the reporter gene are present within a host cell.

Transcription Factors-Promoters for Use in the Invention

Any number of transcription factors that bind to dicarboxylic acid, or are activated to bind to a promoter in response to a signal generated by binding of a dicarboxylic acid to a binding moiety, are suitable for use in the invention.

In some embodiments, the transcription factor can bind a dicarboxylic acid, which results in binding of the transcription factor to a cognate promoter and activation of a gene that is operably linked to the promoter. Transcription factors that bind dicarboxylic acids include the transcription factor PcaR and homologs, see, e.g., FIG. 1.

In one embodiment, a transcription factor used in the invention is a PcaR transcription factor. A PcaR transcription factor can directly bind a dicarboxylic substrate and regulate transcription mediated by promoters such as the $P_{PcaR}$ and $P_{PcaIJ}$ promoters. Thus, in such embodiments, the dicarboxylic binding moiety is contained within the transcription factor itself and no additional sensory polypeptides are required for function. PcaR binds C6 dicarboxylic acids (beta-keto hexanedioic acid and hexanedioic acid) substrates. PcaR and PcaR-responsive promoters are known in the art (see, e.g., Guo Z, et al. "PcaR-mediated activation and repression of pca genes from *Pseudomonas putida* are propagated by its binding to both the −35 and the −10 promoter elements." *Mol. Microbiol.* 32(2):253-63 (1999), incorporated by reference).

An example of a PcaR polypeptide sequence from *Pseudomonas putida* is provided in SEQ ID NO:6. PcaR polypeptides that can be employed also include variants and homologs of the PcaR polypeptide sequence set forth in SEQ ID NO:6. Thus, a PcaR transcription factor polypeptide may have an amino acid sequence that has at least 60% identity, typically at least 70%, 75%, 80%, 85%, 90%, 91%, 92%, 93%, 94%, 95%, 96%, 97%, 98% or 99%, or greater, amino acid sequence identity, preferably over a region of at least 100 or more amino acids, or at least 200 or more amino acids, or over the length of the entire polypeptide, to an amino acid sequence of SEQ ID NO:6. Examples of PcaR amino acid sequences are provided in FIG. 1. One of skill in the art understands in view of this disclosure that variants can also be employed, e.g., using the known sequences as guidance for selecting amino acid substitutions that will not result in loss of function. PcaR transcription factors for use in the invention comprise an IclR helix-turn-helix domain that is important for recognition of the PcaR operator site. PcaR polypeptides also comprise other functional domains, e.g., a region that plays a role in substrate recognition. An example of a helix-turn-helix domain of a PcaR polypeptide is indicated in the illustrative sequence SEQ ID NO:6, shown below, by an underline. A recognition domain that maps to the IclR family of transcription regulators is shown in italics:

MSDETPANESANPESARPAAPALAPPIVASPAKRIQAFTGDPDFMT<u>SLA</u>

<u>RGLAVIQAFQERKRHLTIAQISHRTEIPRAAVRRCLHTLIKLGYATTDG</u>

RTYSLLPKVLTLGHAYLSSTPLAISAQPYLDRISDQLHEAANMATLEGD

DILYIARSATVER*LISVDLSVGGRLPAYCTSMGRILLAAMDDTSLREYL*

*DRADLKARTSRTLNDAESLFACIQQVRAQGWCVVDQELEQGLRSIAVPI*

*YDASGQVLAALNVSTHVGRVTRSELEQRFLPILLAASRDLCHQLFG*

In some embodiments, a PcaR transcription factor for use in the invention is naturally present in a host cell. In other embodiments, a host cell is engineered to express a heterologous transcription factor by introducing an expression cassette comprising a nucleic acid sequence encoding the transcription factor into the host cell.

The PcaR transcription factor can bind to a number of promoters and activate expression of a gene operably linked to the promoter. Examples of PcaR-responsive promoters suitable for use in accordance with the invention are provided in SEQ ID NOs. 7, 8, 16, and 17.

In some embodiments, a PcaR-responsive promoter for use in the invention, typically comprises one or more of the operator sequences GTTTGTTCGATAATCGCACGAACG, (SEQ ID NO:28), GCTCGCACATCGCAC (SEQ ID NO:29), and/or AGTTCGATAATCGCAC (SEQ ID NO:30). Point mutations can be present in these operator sequences, e.g., the biosensors described in Example 5 contain the operator sequences GTTTGTTCGATAATCGCACGAACC (SEQ ID NO:31) and GCTCGCAGATCGCAC (SEQ ID NO:32) (point mutations are indicated in bold type). In some embodiments, the promoter is at least 90% identical to the promoter sequence shown in SEQ ID NO:7, 8, 16, or 17. In some embodiments, the promoter comprises a subsequence of SEQ ID NO:7, 8, 16, or 17 that comprises 25, 30, 25, 40, or 45, or more, contiguous nucleotides of SEQ ID NO:7, SEQ ID NO:8, SEQ ID NO:16, or SEQ ID NO:17.

Two-Component Transcription Factor Dicarboxylic Acid Sensor

In some embodiments, the transcription factor employed in a dicarboxylic acid sensor of the invention is responsive to a dicarboxylic acid, but does not itself bind a dicarboxylic acid. Instead, a sensing protein binds to the dicarboxylic acid and then modifies the transcription factor so that the transcription factor binds to a cognate promoter and activates expression of a reporter gene. In some embodiments, the dicarboxylic acid binding moiety is a transmembrane polypeptide.

In one embodiment, a two-component systems comprises a membrane-associated sensor (sensory histidine kinase DcuS) and a cytosolic response regulator (DcuR). DcuS detects C4-dicarboxylic acids (succinate and fumarate) in the environment, which results in autophosphorylation of a histidine residue. For example, with *E. coli* DcuS-DcuR, this phosphoryl group is subsequently transferred to the DcuR aspartic acid residue D56, activating DcuR. When activated, DcuR binds to a number of promoters and either activates or represses transcription of downstream genes. DcuS and DcuR function has been well characterized (see, e.g., Abo-Amer A E, et al. "DNA interaction and phosphotransfer of the C4-dicarboxylate-responsive DcuS-DcuR two-component regulatory system from *Escherichia coli*."*J Bacteriol*. 186(6):1879-1889 (2004); Janausch I G, et al. "Phosphorylation and DNA binding of the regulator DcuR of the fumarate-responsive two-component system DcuSR of *Escherichia coli*."*Microbiology* 150:877-883 (2004); Davies S J, et al. "Inactivation and regulation of the aerobic C(4)-dicarboxylate transport (dctA) gene of *Escherichia coli*." *J Bacteriol* 181(18):5624-35 (1999); Zientz E, et al. "Fumarate regulation of gene expression in *Escherichia coli* by the DcuSR (dcuSR genes) two-component regulatory system." *J Bacteriol* 180(20):421-5 (1998); and Golby P, et al. "Identification and characterization of a two-component sensor-kinase and response-regulator system (DcuS-DcuR) controlling gene expression in response to C4-dicarboxylates in *Escherichia coli*." *J Bacteriol* 181(4):1238-48 (1999). See, also Janausch et al., "Function of DcuS from *Escherichia coli* as a Fumarate-stimulated Histidine Protein Kinase I", *J. Biol. Chem.* 277:39809-39814, 2002.

An example of a DcuS polypeptide dicarboxylic acid binding protein sequence from *E. coli* is provided in SEQ ID NO:1. DcuS polypeptides that can be employed in accordance with the invention also include variants and homologs of the polypeptide sequence set forth in SEQ ID NO:1. Thus, a DcuS histidine kinase sensory polypeptide may have an amino acid sequence that has at least 60% identity, typically at least 70%, 75%, 80%, 85%, 90%, 91%, 92%, 93%, 94%, 95%, 96%, 97%, 98% or 99%, or greater, amino acid sequence identity, preferably over a region of at least 400, or 500 or more amino acids, or over the length of the entire polypeptide, to an amino acid sequence of SEQ ID NO:1. DcuS histidine kinases have been characterized in the art. See, e.g., Abo-Amer et al., supra, and references cites therein, which along with other characterization of the DcuS-DcuR system in *E. coli*, describe the domain structure of DcuS and related proteins; see, also Zientz et al, and Golby et al, supra, which describe the DcuS-DcuR system and the topological organization of the DcuS protein.

An example of a DcuR transcription factor that functions in the two-component system is DcuR. An example of a DcuR polypeptide sequence from *E. coli* is provided in SEQ ID NO:2. DcuR polypeptides that can be employed in accordance with the invention also include variants and homologs of the polypeptide sequence set forth in SEQ ID NO:2. Thus, a DcuR transcription factor polypeptide may have an amino acid sequence that has at least 60% identity, typically at least 70%, 75%, 80%, 85%, 90%, 91%, 92%, 93%, 94%, 95%, 96%, 97%, 98% or 99%, or greater, amino acid sequence identity, preferably over a region of at least 200 or more amino acids, or over the length of the entire polypeptide, to an amino acid sequence of SEQ ID NO:2. DcuR transcription factors have been characterized in the art. See, e.g., Janausch, et al., 2002, 2004 supra, which describe the DcuS-DcuR system and DNA binding of DcuR. As noted, the D56 residue of SEQ ID NO:2 is important for function.

In some embodiments, a DcuR and/or DcuS protein for use in the invention is naturally present in a host cell. In other embodiments, a host cell is engineered to express a DcuR and/or DcuS by introducing an expression cassette comprising nucleic acids encoding a desired DcuR and/or DcuS protein into the host cell. Nucleic acids encoding DcuS and DcuR may be present in one expression construct or may be introduced as separate constructs.

A DcuS transcription factor can bind to a number of promoters and activate expression of a gene operably linked to the promoter. Examples of DcuS-responsive promoters are provided in SEQ ID NOs: 3, 4, and 5.

In some embodiments, a DcuR-responsive promoter for use in the invention typically comprise one or more of the operator sequences TTTTAATTTCAAAA (SEQ ID NO:33), TAATTAACTATTAT (SEQ ID NO:34), TACAAAACTT-TAAA (SEQ ID NO:35), or TAGTAATTAAATTA (SEQ ID NO:36). In some embodiments, the promoter is at least 70% identical, or at least 80%, at least 90%, or at least 95% identical, to the promoter sequence shown in SEQ ID NO:3. In some embodiments, the promoter is 90% identical to the subsequence of SEQ ID NO:3 upstream of the transcription start site and comprises the operator sequences shown in SEQ ID NO:3. In some embodiments, the promoter is at least 70% identical, or at least 80%, at least 90%, or at least 95% identical, to the promoter sequence shown in SEQ ID NO:4. In some embodiments, the promoter comprises at least 25, 30, 25, 40, or 45, or more, contiguous nucleotides of the region of SEQ ID NO:4 upstream of the transcription initiation site and comprises the operator sequence shown in SEQ ID NO:4. In some embodiments, the promoter is at least 70% identical, or at least 80%, at least 90%, or at least 95% identical, to the promoter sequence shown in SEQ ID NO:5. In some embodiments, the promoter comprises at least 25, 30, 25, 40, or 45, or more, contiguous nucleotides of the region of SEQ ID NO:5 upstream of the transcription initiation site and comprises the operator sequence shown in SEQ ID NO:5. Promoters to which DcuR binds, following phosphorylation by DcuS, have been described in the references cited above; see, e.g., Janausch et al., 2002, 2004, supra.

In some embodiments, a transcription factor biosensor system of the invention comprises a two-component system, a sensory histidine kinase DctB and a transcription factor DctD. DctB and DctD have been characterized in the art (e.g., Davies et al. "Inactivation and Regulation of the Aerobic $C_4$-Dicarboyxlate Tansport (dctA) gene of *Escherichia coli, J. Bacteriol.* 181:5624-5635, 1999; Nan et al., "From signal perception to signal transduction: ligand induced dimeric switch of DctB sensory domain in solution" *Molec. Microbiol.* 75:1481-1494, 2010; Giblin et al., "Modular structure of the *Rhizobium meliloti* DctB protein", *FEMS Microbiol Letters* 139:19-25, 1996; Wang et al. "A conserved region in the σ54-dependent activator DctD is involved in both binding and to RNA polymerase and coupling ATP hydrolysis to activation" *Molec. Microbiol.* 26:373-386, 1997; Xu et al. "Purification and Characterization of the AAA+ Domain of *Sinorhizobium meliloti* DctD, a $\sigma^{54}$-Dependent Transcriptional Activator" *J. Bacteriol.* 186:3499-3507, 2004).

An example of a DctD polypeptide sequence from *Sinorhizobium meliloti* is provided in SEQ ID NO:10. DctD polypeptides that can be employed in accordance with the invention also include variants and homologs of the polypeptide sequence set forth in SEQ ID NO:10. Thus, a DctD transcription factor polypeptide may have an amino acid sequence that has at least 60% identity, typically at least 70%, 75%, 80%, 85%, 90%, 91%, 92%, 93%, 94%, 95%, 96%, 97%, 98% or 99%, or greater, amino acid sequence identity, preferably over a region of at least 300 or 400 or more amino acids, or over the length of the entire polypeptide, to an amino acid sequence of SEQ ID NO:10. DctD transcription factors and structurally important domains and amino acid residues have been characterized in the art (see, e.g., Xu et al, 2004, supra; Wang et al, 1997, supra).

An example of a dicarboxylic acid binding protein that functions in the two-component system is DctB. An example of a DctB polypeptide sequence from *Sinorhizobium meliloti* is provided in SEQ ID NO:9. DctB polypeptides that can be employed in accordance with the invention also include variants and homologs of the polypeptide sequence set forth in SEQ ID NO:9. Thus, a DctB dicarboxylic acid binding polypeptide may have an amino acid sequence that has at least 60% identity, typically at least 70%, 75%, 80%, 85%, 90%, 91%, 92%, 93%, 94%, 95%, 96%, 97%, 98% or 99%, or greater, amino acid sequence identity, preferably over a region of at least 400, 500, or 600 or more amino acids, or over the length of the entire polypeptide, to an amino acid sequence of SEQ ID NO:9. DctB histidine kinase and structurally important domains and amino acid residues have been characterized in the art (see, e.g., Nan et al., 2010; and Giblin et al, 1996, supra).

In some embodiments, a DctD transcription factor and/or a DctB dicarboxylic acid binding protein for use in the invention is naturally present in a host cell. In other embodiments, a host cell is engineered to express the DctD and or DctB protein by introducing an expression cassette comprising a nucleic acid sequence encoding the DctD and/or DctB protein into the host cell. Nucleic acids encoding DctD and DctB may be present on one expression construct or may be introduced into a host cell as separate constructs.

A DctD transcription factor can bind to a number of promoters and activate expression of a gene operably linked to the promoter. An example of a DctD-responsive promoter is provided in SEQ ID NO:11.

In some embodiments, a DctD-responsive promoter for use in the invention typically comprise one or both of the operator sequences ACTGGTGCATCTTTTCGGCCAGG (SEQ ID NO:37) or TGTGCGGAAATCCGCACA (SEQ ID NO:38).

In some embodiments, the promoter is at least 70% identical, or at least 80%, at least 90%, or at least 95% identical, to the promoter sequence shown in SEQ ID NO:11. In some embodiments, the promoter is at least 90% identical to a 55 nucleotide subsequence of SEQ ID NO:11 that comprises both of the operator sequences ACTGGTGCATCTTTTCG-GCCAGG (SEQ ID NO:39) and TGTGCGGAAATCCG-CACA (SEQ ID NO:40).

RNA Polymerase

A transcription factor biosensor of the invention responds to the presence of a dicarboxylic acid by activating transcription of a reporter gene. The transcription of the reporter gene is performed by an RNA polymerase. Thus, detection methods for dicarboxylic acids using a biosensor of the invention is performed in an environment in which an RNA polymerase that is capable of being activated by the transcription factor is present.

In some embodiments, e.g., using a DctB-DctD biosensor, a $\sigma^{54}$ RNA polymerase is activated. In some embodiments, e.g., using DcuS-DcuR or PcaR-based biosensors, the transcription factor does not directly interact with a RNA polymerase, but binds to a promoter and allows the $\sigma^{70}$ subunit of the RNA polymerase to bind to the $\sigma^{70}$ recognition sequence on the promoter. The sigma subunits of RNA polymerase specifically bind to DNA sequence elements and are responsible for differential gene expression. Sigma factor $\sigma^{70}$ associates with the core RNA polymerase to transcribe housekeeping genes. The complex E-$\sigma^{70}$ alone can be sufficient to catalyze the open promoter complex and allow RNA transcription.

In some embodiments, a dicarboxylic acid transcription factor biosensor system of the invention, e.g., a DctB-DctD biosensor system, comprises a $\sigma^{54}$ or has the capability of expressing $\sigma^{54}$. Any $\sigma^{54}$ can be used to initiate transcription from the promoter. Examples of suitable $\sigma^{54}$ polypeptides are provided in SEQ ID NOs. 12-15.

The system or host cell of the present invention can comprise a nucleic acid encoding any of the suitable $\sigma^{54}$. In some embodiments of the invention, a nucleic acid encoding any of the suitable $\sigma^{54}$ is operatively linked any promoter that is capable of driving expression in the system or host cell. In some embodiments, the promoter operatively linked to the suitable $\sigma^{54}$ is constitutively expressed, or is a native promoter.

Host Cells

The present invention provides for a modified host cell comprising a transcription factor a dicarboyxlic acid binding moiety and promoter operatively linked to a reporter gene.

In some embodiments of the invention, the host cell is a bacterium. In some embodiments of the invention, the bacterium is a Gram-negative β-proteobacterium. In some embodiments of the invention, the bacterium is an enteric bacterium. In some embodiments of the invention, the bacterium is of the genus *Bacillus, Planctomyces, Bradyrhizobium, Rhodobacter, Rhizobium, Myxococcus, Klebsiella, Azotobacter, Escherichia, Salmonella, Pseudomonas, Caulobacter, Chlamydia, Acinetobacter, Sinorhizobium, Enterococcus, Clostridium*, and *Vibrio*. In some embodiments of the invention, the bacterium is *E. coli*.

In some embodiments, the host cell has been recombinantly engineered to produce a dicarboxylic acid (see, e.g., WO2009/121066 and PCT Application No. PCT/US2011/058660, which are incorporated herein by reference).

The nucleic acid sequences encoding a transcription factor biosensor system of the invention can be introduced into a host cell in which the corresponding gene, or genes, have been inactivated. Inactivation can be performed using any known technique, e.g., by recombination, mutagenesis and the like. Similarly, in some embodiments, a native promoter to which the transcription factor binds may be deleted or otherwise mutagenized to prevent transcription factor binding to the native sequence. In some embodiments the host cell may also have additional promoters inactivated where the promoters that are responsive to the dicarboxylic acid-activated transcription factor employed in the sensor. For example, in an embodiment in which a DcuS-DcuR sensor is employed with a DcuB promoter linked to a reporter gene, the endogenous DcuS and DcuR genes may be knocked out, as well as the endogenous DcuB promoter, as well as other promoters that are responsive to the transcription factor, e.g., the DctA and FrdA promoters.

Reporter Genes

In some embodiments of the invention, the reporter gene encodes a beta-galactosidase, a fluorescent protein, e.g., a green fluorescent protein, or an antibiotic resistance protein. In some embodiments, the reporter is an antibiotic resistance gene that confers resistance to the antibiotic. In some embodiments of the invention, the reporter gene is cat, tet, or bla. The reporter gene can be used as a positive selection or as a negative selection. Positive selection occurs when the increased expression of the gene product of the reporter gene increases the probability that the host cell would remain viable and complete doubling. Examples of reporter genes that confer positive selection are antibiotic resistance genes that confer resistance to an antibiotic to the host cell when the host cell is cultured or grown in a culture containing the antibiotic. An example of such as is a β-lactamase, encoded by the bla gene. Other examples of antibiotic resistance genes include tet. Other examples of reporter genes that confer positive selection are genes encoding enzymes that are required by the host cell to metabolize a specific nutrient source which is required by the host cell in order to remain viable and double. Negative selection occurs when the increased expression of the gene product of the reporter gene decreases the probability that the host cell would remain viable and complete doubling. Examples of reporter genes that confer negative selection are genes that when expressed, inhibit resistance to an antibiotic of the host cell when the host cell is cultured or grown in a culture containing the antibiotic. An example of such as inhibitor is a β-lactamase inhibitor, such as clavulanic acid, which inhibits a β-lactamase, e.g., ampicillin.

Preparation of Recombinant Expression Vectors

Once the promoter sequence and the coding sequence for the gene of interest (e.g., a transcription factor, a sensor protein, or, optionally, a polymerase gene) are obtained, the sequences can be used to prepare an expression cassette for expressing the gene of interest in a host cell.

In some embodiments, a nucleic acid sequence encoding a dicarboxylic acid-sensitive transcription factor, or a sequence nucleic acid encoding a dicarboxylic acid sensing protein and a nucleic acid sequence encoding a transcription factor activated by the sensing protein are introduced into a host cell. In the two component system, the sensor and transcription factor may be present on the same nucleic acid molecule or may be separately introduced into a host cell. The host cell is also engineered to contain a reporter construct containing the transcription factor-sensitive promoter operably linked to a reporter gene. In some embodiments, a polymerase may also be introduced into a host cell. In some embodiments of the present invention, the nucleic acid encoding the sequences of interest are each introduced independently on a vector into a host cell or are each independently integrated into a chromosome. In other embodiments, all of the sequences of interest are contained in a single vector or integrated at a single site in the chromosome. The vector can be an expression vector such as a plasmid. In some embodiments of the present invention, the vector is capable of stable maintenance in a host cell.

One of skill understands that expression constructs may contain other sequences necessary for expression of a protein. Thus, a recombinant nucleic acid can also comprise promoter sequences for transcribing a transcription factor, sensor protein, or optionally, a polymerase, in a suitable host cell. In some embodiments, the promoter sequence that governs expression of the transcription factor and/or sensor polypeptide is an inducible promoter, e.g., an arabinose promoter, or other inducible promoter. In some embodiments, the promoter is a constitutive promoter. The recombinant nucleic acid can also comprise sequences sufficient for having the recombinant nucleic acid stably replicate in the host cell. The recombinant nucleic acid can be replicon capable of stable maintenance in a host cell. In some embodiments, the replicon is a plasmid. The present invention also provides expression vectors encoding for the expression of one or more components of a biosensor of the present invention.

Selectable markers can also be included in the recombinant expression vectors, it being understood, in this context, that a selectable marker is not the reporter gene used in a biosensor of the invention. For example, an ampicillin selectable marker, encoded by the bla gene, is present on the vector (e.g. plasmid S1 or S3) and is under control of a constitutive promoter; ampicillin resistance is used to maintain the plasmid in the host cell and not to measure biosensor activation. A variety of markers are known that are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity.

The nucleic acids having nucleotide sequences described herein, or a mixture of such nucleic acids, can be cloned into one or more recombinant vectors as individual cassettes, with separate control elements or under the control of a single promoter. Methods for introducing the recombinant vectors of the present invention into suitable hosts are known to those of skill in the art and typically include the use of $CaCl_2$ or other agents, such as divalent cations, lipofection, DMSO, protoplast transformation, conjugation, and electroporation.

As understood in the art, nucleic acid sequence to be expressed in a particular host cell may also be codon optimized to use codons preferred by the host species.

Methods of the Present Invention

The present invention provides for a method for sensing a dicarboxylic acid. In some embodiments, the dicarboxylic acid is one or more of a C4-C14 dicarboxylic acid. In some embodiments, the dicarboxylic acid is a C4 (butanedioic acid), C5 (pentanedioic acid) C6 hexanedioic acid), C7 (heptanedioic acid), C8 (octanedioic acid), C9 (nonanedioic acid), C10 (decanedioic acid), C11 (undecanedioic acid), C12 (dodecanedioic acid), C13 (tridecanedioic acid), or C14 (tetradecanedioic acid).

In some embodiments of the invention, the detecting step comprises detecting, e.g., measuring the amount of a gene product such as a fluorescent reporter gene. In some embodiments of the invention, the gene product of the reporter gene influences the growth rate of a host cell comprising the components of a dicarboxylic acid transcription factor biosensor of the invention. In some embodiments, the gene product of the reporter gene causes the modified host cell to become resistant or sensitive to a compound. For example, in some embodiments, the reporter gene is an antibiotic resistance gene, e.g., a tet gene, where the presence of a dicarboxylic acid in the culture medium induces antibiotic resistance such that the host cell exhibits improved growth in the presence of a dicarboxylic acid when the antibiotic is present. In some embodiments, a host cell that comprises the components of a transcription factor biosensor of the invention is a host cell that is capable of producing a dicarboxylic acid.

The present invention provides for a method for screening or selecting a host cell that produces a C4-C14 dicarboxylic acid comprising: (a) providing a modified host cell of the present invention, (b) culturing the host cell, and (c) screening or selecting the host cell based the expression of the reporter gene by the host cell.

In some embodiments of the invention, the method for screening or selecting a host cell that produces a C4-C14 dicarboxylic acid comprises: (a) providing a plurality of modified host cells of the present invention wherein the modified host cells of different modification are in separate cultures, (b) culturing each separate culture of host cell, (c) screening or selecting the host cell based the expression of the reporter gene by the host cell, and (d) comparing the expression of the reporter genes of the separate cultures. In some embodiments, the (d) comparing step comprises identifying one or more cultures, and/or the corresponding host cell, that have an increased expression of the gene product of the reporter gene.

In some embodiments, a method of the invention is a method for selecting a host cell that produces a C4-C14 dicarboxylic acid, wherein the selection is a positive selection or a negative selection. When the selection is positive selection, the selecting step selects for host cells that have a higher expression of a reporter gene where expression of the reporter gene increases the probability of remaining viable and doubling. When the selection is negative selection, the selecting step selects for host cells that have a lower expression of the reporter gene where expression of the reporter gene decreases the probability of remaining viable and doubling.

In one embodiment of the present invention, the method for selecting an E. coli host cell that produces a C4-C14 dicarboxylic acid comprises: (a) providing a plurality of modified E. coli host cells of the present invention wherein the modified host cells of different modification are in separate cultures, (b) culturing each separate culture of host cell, (c) selecting the host cell based the expression of the reporter gene by the host cell, and (d) comparing the expression of the reporter genes of the separate cultures, wherein the selecting is a positive selecting.

In another embodiments of the present invention, the method for selecting an E. coli host cell that produces a C4-C14 dicarboxylic acid comprises: (a) providing a plurality of modified E. coli host cells of the present invention wherein the modified host cells of different modification are in separate cultures, (b) culturing each separate culture of host cell, (c) selecting the host cell based the expression of the reporter gene by the host cell, and (d) comparing the expression of the reporter genes of the separate cultures, wherein the selecting is a negative selecting.

EXAMPLES

The following examples are provided to illustrate, but not limit the claimed invention.

Example 1

Dcu2-DcuR Transcription Factor Dicarboxylic Acid Biosensor

This example employs a dicarboxylic acid-responsive two-component system comprised of the E. coli DcuS-DcuR proteins expressed in an E. coli host in which the native genes encoding for the DcuS and DcuR, and the DcuB, DctA, and FrdA promoter have been knocked out (strain JD-diacid). More specifically, the plasmid pDiacid-1 is constructed using a sequence and ligation independent cloning protocol (Li & Elledge, Harnessing homologous recombination in vitro to generate recombinant DNA via SLIC. Nat Meth 4, 251-256, 2007). The E. coli dcuS gene is amplified from E. coli (strain MG1655) chromosome using primers P1 (5'-tttttggtagagaaa-gaggagaaatactagatgagacattcattgccctaccgcatgtta-3'; SEQ ID NO:41) and P2 (5'-tgatcatctagtatttctcctctttctc-tatcatctgttcgacctctccccgtcccaggg-3'; SEQ ID NO:42), and the E. coli dcuR gene is amplified from E. coli (strain MG1655) chromosome using primers P3 (5'-cagatgatagagaaagag-gagaaatactagatgatcaatgtattaattatcgatgacgac-3'; SEQ ID NO:43) and P4 (5'-agttttgttcgggcccaagcttca-gatccttattggcaatattgtttcagtagtgagta-3'; SEQ ID NO:44). The pDcuB promoter is amplified from E. coli (strain MG1655) chromosome using primers P5 (5'-ttcgttttatctgttgtttgtcggt-gaactgtgtttttaatttcaaaacgctaacaaaag-3'; SEQ ID NO:45) and P6 (5% ccctccttatctattctgcg-taataaaatatatttaaattttttgctgaatagatcacagt-3'; SEQ ID NO:46). The resulting PCR products are subsequently assembled using the SLIC protocol with a vector backbone housing a p15a origin of replication, chloramphenicol antibiotic resistance marker, arabinose-responsive pBad promoter, and gene encoding for green fluorescent protein (GFP); forming plasmid pDiacid-1 (FIG. 2).

Host strain JD-diacid is constructed by knocking out the native C4-diacid responsive elements in the E. coli genome using standard protocols described in the literature (Datsenko & Wanner, One-step inactivation of chromosomal genes in Escherichia coli K-12 using PCR products. Proc. Natl. Acad. Sci. USA 97, 6640-6645, 2000). Specifically, E. coli (strain MG1655) chromosomal region from position 4,345,427 to 4,349,866 (containing the dcuB, dcuS and dcuR genes and the pDcuB promoter) are knocked out with an antibiotic resistance cassette. Similarly, the DcuR operator on the pFrdA promoter (position 4,380,531 to 4,380,544) is knocked out.

Figure 6:
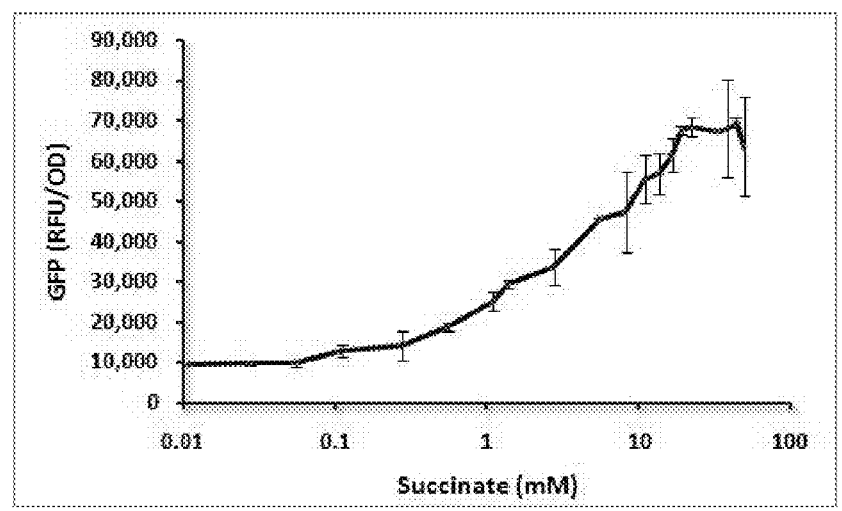
FIG. 6 shows an idealized dose-response curve for a DcuS-DcuR transcription factor dicarboxylic acid biosensor.

The dose-response profile of the pDiacid-1 plasmid using succinate as an inducer is conducted. E. coli strain JD-diacid harboring plasmid pDiacid-1 is cultured overnight in LB media ($Cb^{50}$, 200 rpm, 30° C.). Cultures are then inoculated 1% v/v into fresh media ($Cb^{50}$), grown until final cell densities reached an optical density at 600 nm ($OD_{600}$) of 0.20 and subsequently diluted 1:4 in media containing between 0 and 50 mM succinate to a final volume of 1504 in 96 deep-well plates. The cultures are next grown for 24 hours (200 rpm, 30° C.) at which point the GFP fluorescence and $OD_{600}$ measurements are taken on a fluorometer/spectrophotometer. GFP fluorescence values (relative fluorescent units) are normalized relative to the $OD_{600}$ measurements and plotted versus the succinate concentration. An idealized dose-response curve for a biosensor is provided (FIG. 6).

Example 2

Pseudomonas putida PcaR Transcription Factor Dicarboxylic Acid Sensor

Figure 4:
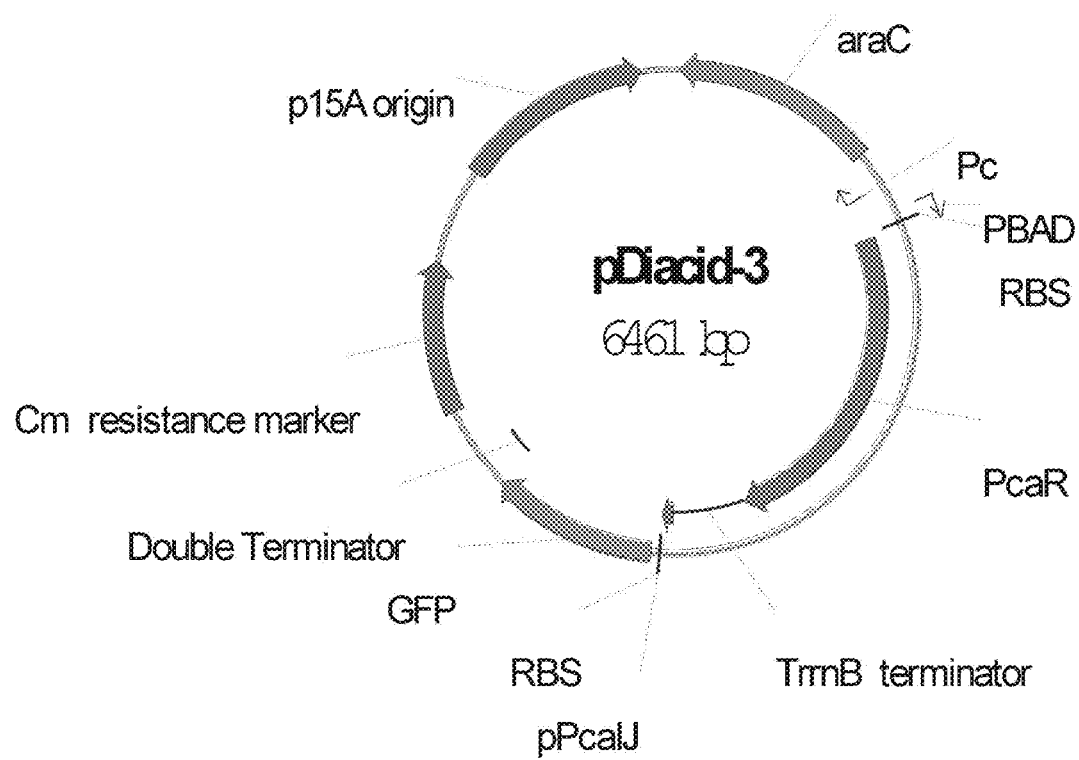
FIG. 4 provides a map of an illustrative plasmid of the invention, which encodes a dicarboxylic acid biosensor of the invention, that comprises nucleic acid sequences a PcaR transcription factor and a green fluorescent protein reporter gene operably linked to a PcaIJ promoter.

The Pseudomonas putida gene pcaR, encoding for the beta-keto hexanedioic acid and hexanedioic acidresponsive transcription factor PcaR, is cloned in place of the dcuS and dcuR genes on plasmid pDiacid-2, forming plasmid pDi-acid-3 (FIG. 4). E. coli colonies harboring the pDiacid-3 plasmid are cultured into early exponential phase, and PcaR expression is induced with 1 mM arabinose. The culture is allowed to grown for an additional 4-6 hours until reaching late exponential phase. The GFP fluorescence signal from individual cells is measured on a fluorescence activated cell sorter (FACS), and those cells exhibiting improved GFP fluorescence above the median are sorted. This resulting population of cells exhibiting high-GFP fluorescence exhibit improved hexanedioic acid production. Specific genetic changes resulting in improved hexanedioic acid production are then identified by sequencing the host organism genome, or by targeted sequencing of individual nucleic acid sequences that are believed to influence hexanedioic acid production.

Example 3

TetA Gene Reporter

Figure 5:
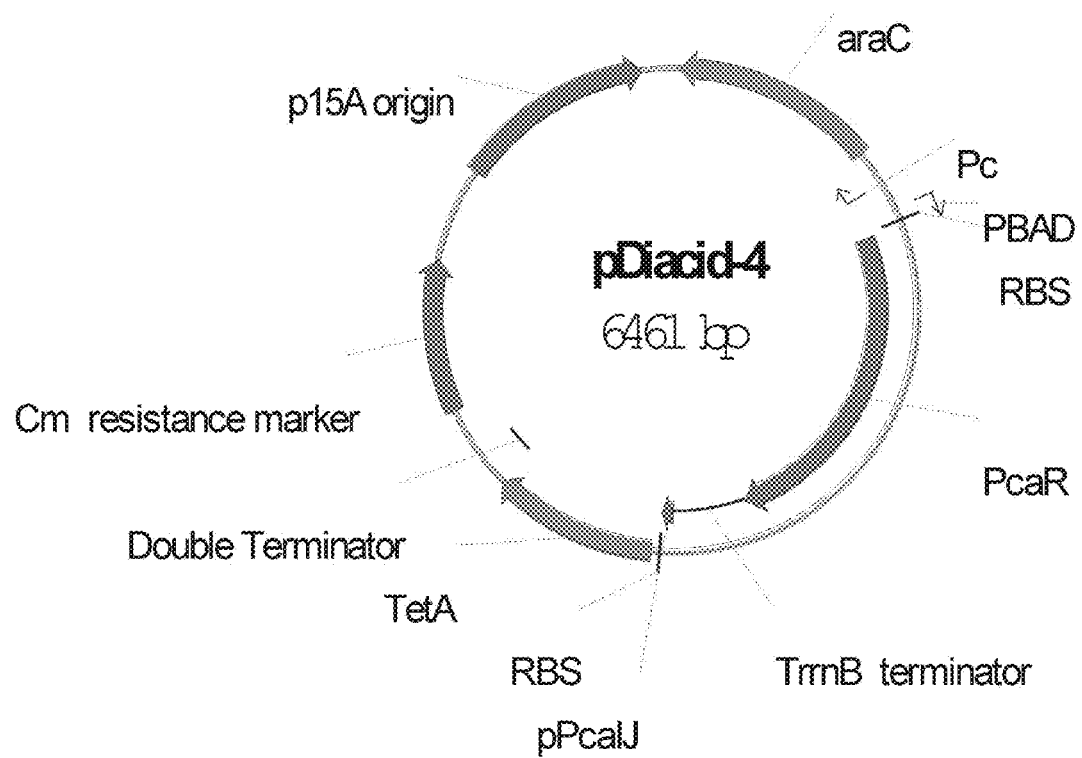
FIG. 5 provides a map of an illustrative plasmid of the invention comprising a tetA gene encoding the tetracycline resistance conferring protein TetA. In this example, the tetA gene replaces the GFP reporter gene in plasmid pDiacid-3 (FIG. 4), forming plasmid pDiacid-4.

The tetA gene as a reporter encoding the tetracycline resistance protein TetA, is cloned in place of the GFP reporter gene in plasmid pDiacid-3, forming plasmid pDiacid-4 (FIG. 5). When plasmid pDiacid-4 is transformed into an E. coli strain capable of hexanedioic acid production, and PcaR expression is induced with arabinose, the degree of tetracycline resistance corresponds to the host strains hexanedioic acid productivity. Either the specific growth rate of the E. coli cell culture or the final cell culture density (the optical density as measured by a spectrophotometer) is monitored to identify improved hexanedioic acid production strains.

Example 4

E. coli DcuS-DcuR Transcription Factor Dicarboxylic Acid Biosensor using a TetA Reporter This example describes a dicarboxylic acid-responsive two-component system of the invention comprised of the E. coli DcuS-DcuR proteins expressed in a wild type E. coli K12 host. More specifically, plasmid S4 was constructed. Plasmid S4 comprises a tetA gene encoding for a tetracycline resistance protein under control of the $P_{DctA}$ promoter on an E. coli vector backbone with ampicillin resistance marker and ColE1 origin of replication; the $P_{DctA}$ promoter was polymerase chain reaction (PCR) amplified from the E. coli K12 genome and aligns to nucleotides 3681652-3681471 of the E. coli MG1655 genome. Similarly, plasmids S5 and S6 were constructed. Plasmids S5 and S6 comprise a tetA gene under control of the $P_{DcuB}$ promoter on identical vector backbones to S4. Plasmid S5 comprises promoter $P_{DcuB\#21}$, which was PCR amplified from E. coli K12 and aligns to nucleotides 4347337-4346905 of the E. coli MG1655 genome. Plasmid S6 comprises promoter $P_{DcuB\#22}$, which was PCR amplified from E. coli K12 and aligns to nucleotides 4347337-4347064 of the E. coli MG1655 genome. All plasmids were constructed from the PCR-amplified nucleic acids and appropriate vector backbones using standard cloning techniques.

E. coli strain K12 was transformed with plasmids S4, S5, or S6 and individual colonies isolated from LB agar plates ($Cb^{50}$). Colonies were grown in 25 ml LB broth ($Cb^{50}$) until reaching an optical density at 600 nm ($OD_{600}$) of approximately 0.50, at which point cell stocks were prepared and stored at −80° C.; cell stocks comprised 0.5 ml cell culture and 0.5 ml of 50% v/v glycerol in water.

Biosensor experiments were performed with butanedioic acid. An aliquot of biosensor cell stock was thawed and used to inoculate 50 ml of LB medium ($Cb^{50}$) in a 250 ml, baffled Erlenmeyer flask. Cultures were incubated for 2 hours at 37° C.; subsequently, 0.6 ml biosensor culture was added to 48-well plates prepared with 2.3 ml LB medium ($Cb^{50}$) supplemented with tetracycline and butanedioic acid at the desired concentration (n=4). Plates were grown at 30° C. on an orbital titer plate shaker (Lab Line Instruments). Following 12 hours incubation, 200 µl samples were taken for $OD_{600}$ measurement (Tecan Ultra).

Figure 8:
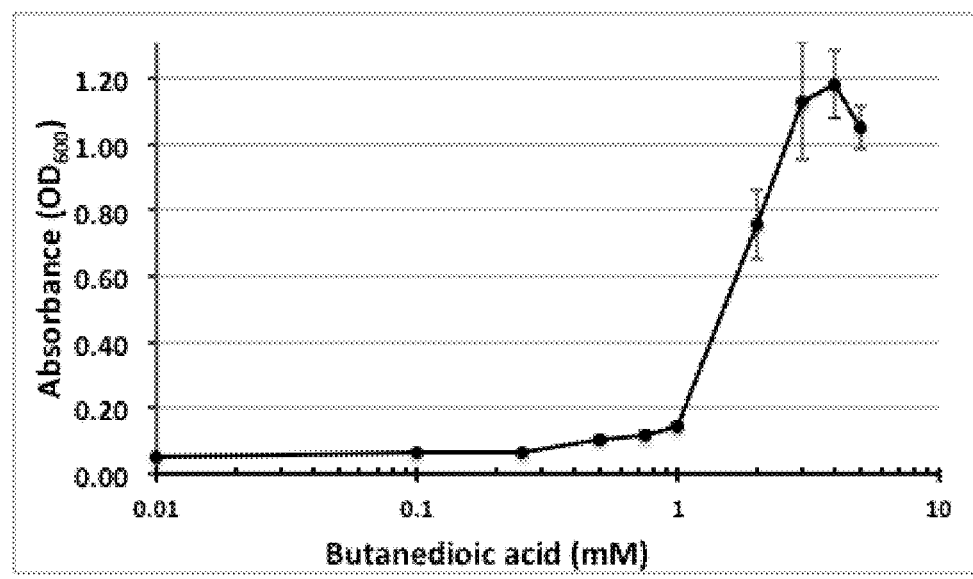
FIG. 8 shows a dose-response curve for an *E. coli* DcuS-DcuR two-component system based dicarboxylic acid biosensor of the invention using promoter PDctA. The X-axis is the concentration of exogenous dicarboxylic acid supplemented to the growth medium; the Y-axis is the cell culture density (OD600) after 12 hours growth in medium supplemented with 25 µg/ml tetracycline. The *E. coli* strain "DctA" comprises plasmid S4 and produces the tetracycline resistance protein upon exogenous addition of butanedioic acid. The DctA biosensor displayed butanedioic acid-dependent increases in tetracycline resistance as measured by the increase in OD600 with the increase in concentration of exogenously added dicarboxylic acid.

Biosensor cultures harboring either S5 or S6 plasmids (i.e., constructs based on $P_{DcuB\#21}$ and $P_{Dcub\#22}$ promoters, respectively) grew under all butanedioic acid concentrations tested. This result indicated the $P_{DcuB}$ promoters tested in these constructs expressed a sufficient level of TetA protein to enable growth in 25 µg/ml tetracycline in the absence of exogenously added butanedioic acid. Thus, the S5 and S6 plasmids were not suitable for application as butanedioic acid biosensors. In contrast, biosensor culture harboring plasmid S4 displayed a dose-dependent response using exogenously added butanedioic acid (FIG. 8). The dynamic range was over 1.2 $OD_{600}$ units with a linear range of response between 1 mM and 5 mM exogenously added butanedioic acid. Thus, construct S4 and the corresponding biosensor strains were well suited for detection of exogenously added butanedioic acid.

Example 5

Pseudomonas putida PcaR Transcription Factor Dicarboxylic Acid Biosensor Using TetA Reporter Three plasmids were used to characterize biosensor response to exogenously added butanedioic acid, pentanedioic acid, hexanedioic acid and heptanedioic acid. The constructed plasmids employ the beta-keto hexanedioic acid and hexanedioic responsive transcription factor, PcaR, and the PcaR-responsive promoters, $P_{PcaR}$ (SEQ ID NO: 16) and $P_{PcaIJ}$ (SEQ ID NO:17), from Pseudomonas putida. Plasmid 51 harbors the P. putida gene pcaI under transcriptional control of it native $P_{PcaIJ}$ promoter on an E. coli vector backbone with ampicillin resistance marker and ColE1 origin of replication. Plasmid S3 harbors the tetA tetracycline resistance gene under control of the $P_{caIJ}$ promoter on an E. coli vector backbone with ampicillin resistance marker and ColE1 origin of replication. Plasmid S2 harbors the pcaR transcription factor gene under control of its native $P_{PcaR}$ promoter on an E. coli vector backbone comprising a chloramphenicol resistance marker and pSC101 origin of replication. The design was based on the following rationale: co-transformation of plasmids S1/S2 into an E. coli host results in a strain expressing the pcaI gene product following supplementation of the growth medium with hexanedioic acid, and the strain should not exhibit a hexanedioic acid-dependent increase in tetracycline resistance; thus, the S1/S2 plasmid combination is a negative control. Co-transformation of plasmids S3/S2 into an E. coli host results in a strain expressing the tetA gene product following supplementation of the growth medium with hexanedioic acid, and the strain should exhibit a hexanedioic acid-dependent increase in tetracycline resistance; thus, the S3/S2 plasmid combination results in a functional dicarboxylic acid biosensor.

Nucleic acids encoding for expression of $P_{PcaR}$, $P_{pcaI}$, PcaI, and PcaR were synthesized (Bioneer) based on the P. putida KT2440 genome sequence; the biosensor vectors were than constructed by polymerase chain reaction (PCR) amplification of the nucleic acids and subsequent cloning into E. coli expression vectors. The plasmids were transformed into chemically competent E. coli DH10b and the resulting clones plated on Luria-Bertani (LB) agar plates containing 50 µg/ml of the appropriate antibiotic (carbenicillin, $Cb^{50}$, or chloramphenicol, $Cm^{50}$). Individual colonies were grown overnight in 3 ml LB medium supplemented with appropriate antibiotic and the sequences of purified plasmids verified (Quintara Biosciences).

E. coli strain K12 was co-transformed with either plasmids S1/S2 or S3/S2 and individual colonies isolated from LB agar plates (Cb$^{50}$, Cm$^{50}$). Colonies were grown in 25 ml LB broth (Cb$^{50}$, Cm$^{50}$) until reaching an optical density at 600 nm (OD$_{600}$) of approximately 0.50, at which point cell stocks were prepared and stored at −80° C.; cell stocks were comprised of 0.5 ml cell culture and 0.5 ml of a 50% v/v glycerol solution.

Biosensor experiments were performed with butanedioic acid, pentanedioic acid, hexanedioic acid, and heptanedioic acid. An aliquot of biosensor cell stock was thawed and used to inoculate 50 ml of LB medium (Cb$^{50}$, Cm$^{50}$) in a 250 ml, baffled Erlenmeyer flask. Cultures were incubated for 2 hours at 37° C.; subsequently, 0.6 ml biosensor culture was added to 48-well plates prepared with 2.3 ml LB medium (Cb$^{50}$, Cm$^{50}$) supplemented with tetracycline and dicarboxylic acid at the desired concentration (n=4). Plates were than grown at 30° C. on an orbital titer plate shaker (Lab Line Instruments). Following 12 hours incubation, 200 μl samples were taken for OD$_{600}$ measurement (Tecan Ultra).

Figure 7:
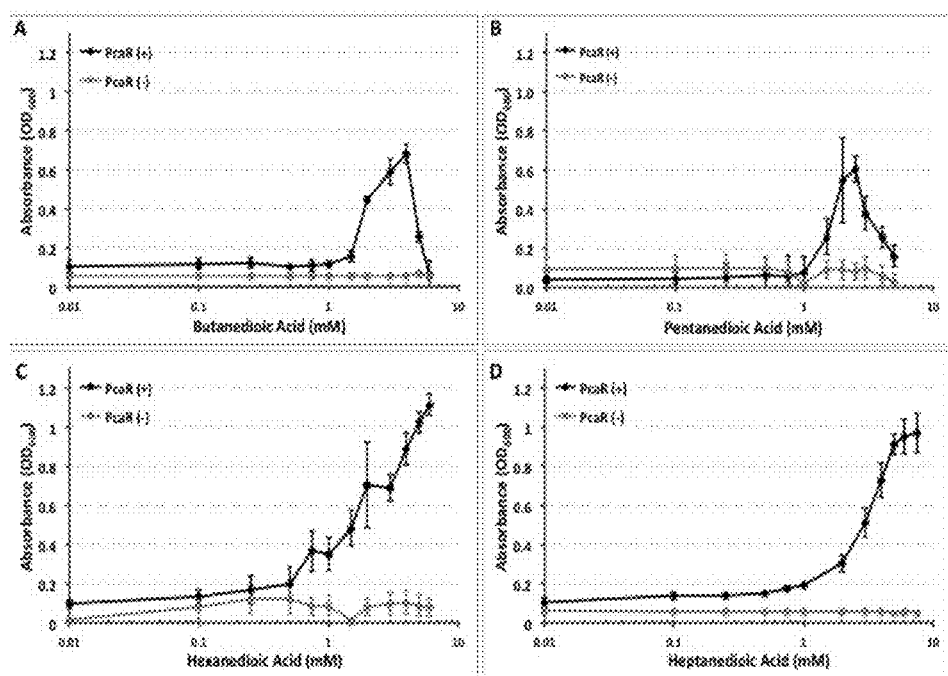
FIG. 7 shows dose-response curves for a *P. putida* PcaR transcription factor-based dicarboxylic acid biosensor of the invention. The X-axis is the concentration of exogenous dicarboxylic acid supplemented to the growth medium; the Y-axis is the cell culture density (OD600) after 12 hours growth in medium supplemented with 25 µg/ml tetracycline. *E. coli* strain "PcaR (+)" comprises plasmids S3/S2 and produces the tetracycline resistance protein upon exogenous addition of dicarboxylic acids. *E. coli* strain "PcaR (−)" comprises plasmids S1/S2 and produces a negative control protein, PcaI, upon exogenous addition of the indicated dicarboxylic acids. The PcaR biosensor displayed dicarboxylic acid-dependent increases in tetracycline resistance as measured by the increase in OD600 with the increase in concentration of exogenously added butanedioic acid (Panel A), pentanedioic acid (Panel B), hexanedioic acid (Panel C), and heptanedioic acid (Panel D).

All biosensor cultures harboring the S1/S2 negative control plasmid combination showed no growth under all conditions tested, demonstrating E. coli would not grow in tetracycline medium supplemented with dicarboxylic acid and tetracycline without a functional biosensor. In contrast, biosensor cultures harboring S3/S2 displayed a dose-dependent response with all four dicarboxylic acids tested (FIG. 7). The highest dynamic range (the maximum difference in OD$_{600}$ values between the fully induced samples and those samples absent dicarboxylic acid supplementation) was observed for heptanedioic acid and hexanedioic acid, indicating the PcaR-based biosensor was most responsive to these longer-chain compounds relative to butanedioic and pentanedioic acids. In the case of hexanedioic acid, a linear response was observed between 0.25-6 mM exogenously added dicarboxylic acid; similarly, in the case of heptanedioic acid, a linear response was observed between 0.5-6 mM exogenously added dicarboxylic acid. For butanedioic and pentanedioic acids, linear responses were observed between 1.5-4 mM and 1-2.5 mM exogenously added dicarboxylic acid, respectively.

It is understood that the examples and embodiments described herein are for illustrative purposes only and that various modifications or changes in light thereof will be suggested to persons skilled in the art and are to be included within the spirit and purview of this application and scope of the appended claims.

All publications, patents, accession numbers, and patent applications cited herein are hereby incorporated by reference in their entirety for all purposes.

EXAMPLES OF SEQUENCES

SEQ ID NO:1 Wild-type E. coli DcuS protein sequence:

```
MRHSLPYRML RKRPMKLSTT VILMVSAVLF SVLLVVHLIY FSQISDMTRD GLANKALAVA
RTLADSPEIR QGLQKKPQES GIQAIAEAVR KRNDLLFIVV TDMQSLRYSH PEAQRIGQPF
KGDDILKALN GEENVAINRG FLAQALRVFT PIYDENHKQI GVVAIGLELS RVTQQINDSR
WSIIWSVLFG MLVGLIGTCI LVKVLKKILF GLEPYEISTL FEQRQAMLQS IKEGVVAVDD
RGEVTLINDA AQELLNYRKS QDDEKLSTLS HSWSQVVDVS EVLRDGTPRR DEEITIKDRL
LLINTVPVRS NGVIIGAIST FRDKTEVRKL MQRLDGLVNY ADALRERSHE FMNKLHVILG
LLHLKSYKQL EDYILKTANN YQEEIGSLLG KIKSPVIAGF LISKINRATD LGHTLILNSE
SQLPDSGSED QVATLITTLG NLIENALEAL GPEPGGEISV TLHYRHGWLH CEVNDDGPGI
APDKIDHIFD KGVSTKGSER GVGLALVKQQ VENLGGSIAV ESEPGIFTQF FVQIPWDGER
SNR
```

SEQ ID NO:2 Wild-type E. coli DcuR protein sequence. Important residue D56 is bolded and enlarged.

```
MINVLIIDDD AMVAELNRRY VAQIPGFQCC GTASTLEKAK EIIFNSDTPI DLILLDIYMQ
KENGLDLLPV LHNARCKSDV IVISSAADAA TIKDSLHYGV VDYLIKPFQA SRFEEALTGW
RQKKMALEKH QYYDQAELDQ LIHGSSSNEQ DPRRLPKGLT PQTLRTLCQW IDAHQDYEFS
TDELANEVNI SRVSCRKYLI WLVNCHILFT SIHYGVTGRP VYRYRIQAEH YSLLKQYCQ
```

SEQ ID NO:3 DcuB promoter and untranslated sequence (pDcuB) The +1 transcription start site is shown in bold italics. The ATG start site of the DcuB protein corresponds to the last three residues in the sequence, which are italicized. The underlined sequences are DcuR operator sites (SEQ ID NOS:33 and 34).

```
GTGTTTTTAATTTCAAAACGCTAACAAAAGTTAATTAACTATTATGTCACCCGCATTATGTGTATTTTA
CCCACAAATGGGTAGATCAGATTAATCTATAAACCTAATGACATCTGCCCTGAGAACAAAAAATAGACCG
```

-continued

ATAAATATCAATAAGATAACAGCAAACAAAACATTAACATCTGCGCAGTACAAACTATAAACCCATCGCC

AGAGAGTCTTTCTCTCTGAAAAAGCCGCTTATCACAGTGCATAAATTTGCCGCTGCTTTAATCAGCCAAT

ATTCACTGTGAGGTATTTGCTAAAGCCGGTAACGACCAAACGGATATTTAGTCAGGCTCTGAAAACAGTT

CATACAAAACAGAACGTGACTGTGATCTATTCAGCAAAAATTTAAATAGGATTATCGCGAGGGTTCACAC

*ATG*

SEQ ID NO:4 DctA Promoter (pDctA) The +1 transcription start site is shown in bold italics. The ATG start site of the DctA protein corresponds to the last three residues in the sequence, which are italicized. The underlined sequence is a DcuR operator site (SEQ ID NO:35).

AAACTGAT<u>TACAAAACTTTAAA</u>AAGTGCTGGTTTGTGCGAGCCAGCTCAAACTTTTTAACCTTTTTGTTT

CAATTATGATCCAGGTACATTTCTGTGATGTTGTCTGGGTGTTATTTTAAGGCC*G*CAGGTACCCCATAAC

CTTACAAGACCTGTGGTTTTACTAAAGGACACCCTA*TG*

SEQ ID NO:5 FrdA promoter (pFrdA) The +1 transcription start site is shown in bold italics. The GTG start site of the FrdA protein corresponds to the last three residues in the sequence, which are italicized. The underlined sequence is a DcuR operator site (SEQ ID NO:36).

ATGGTT<u>TAGTAATTAAATTAA</u>TCATCTTCAGTGATAATTTAGCCCTCTTGCGCACTAAAAAAATCGATCT

CGTCAAATTTCAGACTTATCCATCAGACTATACTGTTGTACCTAT*A*AAGGAGCAGTGGAATAGCGTTCGC

AGACCGTAACTTTCAGGTACTTACCCTGAAGTACGTGGCTGTGGGATAAAAACAATCTGGAGGAATGTC*G*

*TG*

SEQ ID NO: 6 PcaR amino acid sequence:

MSDETPANESANPESARPAAPALAPPIVASPAKRIQAFTGDPDFMTSLARGLAVIQAFQERKRHLTIAQI

SHRTEIPRAAVRRCLHTLIKLGYATTDGRTYSLLPKVLTLGHAYLSSTPLAISAQPYLDRISDQLHEAAN

MATLEGDDILYIARSATVERLISVDLSVGGRLPAYCTSMGRILLAAMDDTSLREYLDRADLKARTSRTLN

DAESLFACIQQVRAQGWCVVDQELEQGLRSIAVPIYDASGQVLAALNVSTHVGRVTRSELEQRFLPILLA

ASRDLCHQLFG

SEQ ID NO:7 PcaR promoter (pPcaR) The transcription start site is in bold italics; PcaR operator sequence (SEQ ID NO:28) is underlined.

AGCGGTCAATTGCGATTATCGGCC<u>GTTTGTTCGATAATCGCACGA</u>*A*CG

GGCGT

SEQ ID NO:8 PcaIJ promoter (pPcaIJ) The transcription start site is in bold italics; PcaR operator sequences (SEQ ID NOS:29 and 30) are underlined.

ACCAGAACT<u>GCTCGCACATCGCAC</u>AAC<u>AGTTCGATAATCGCAC</u>AAA*T*C

CGCT

SEQ ID NO:9 DctB protein sequence

MHHVRMVKLPAEASDPHALRSRARRSWLVFAAVALVLLAAGLLLARDYGRSQALAGLAGQSRIDASLKAS
LLRAVVERQRALPLVLADDAAIRGALLSPDRPSLDRINRKLEALATSAEAAVIYLIDRSGVAVAASNWQE
PTSFVGNDYAFRDYFRLAVRDGMAEHFAMGTVSNRPGLYISRRVDGPGGPLGVIVAKLEFDGVEADWQAS
GKPAYVTDRRGIVLITSLPSWRFMTTKPIAEDRLAPIRESLQFGDAPLLPLPFRKIEARPDGSSTLDALL
PGDSTAAFLRVETMVPSTNWRLEQLSPLKAPLAAGAREAQLLTLAALVPLLALAALLLRRRQVVAMRSAE
ERLARNALEASVEERTRDLRMARDRLETEIADHRQTTEKLQAVQQDLVQANRLAILGQVAAGVAHEINQP
VATIRAYADNARTFLHRGQTVTAAENMESIAELTERVGAITDELRRFARKGHFAAGPTAMKEVVEGALML
LRSRFAGRMDAIRLDLPPDGLQALGNRIRLEQVLINLLQNALEAIGDSEDGAIQVRCEEAAGGIALTVAD
NGPGIAADVREELFTPFNTSKEDGLGLGLAISKEIVSDYGGTIEVESGPSGTTFAVNLKKA

SEQ ID NO:10 DctD protein sequence

MSAAPSVFLIDDDRDLRKAMQQTLELAGFTVSSFASATEALAELSADFAGIVISDIRMPGMDGLALFGKV
LALDPDLPMILVTGHGDIPMAVQAIQDGAYDFIAKPFAADRLVQSARRAEEKRRLVMENRSLRRAAEAAS
EGLPLIGQTPAMERLRQTLKHIADTDVDVLVAGETGSGKEVVATLLHQWSRRRTGNFVALNCGALPETVI
ESELFGHEPGAFTGAVKKRIGRIEHASGGTLFLDEIEAMPPATQVKMLRVLEAREITPLGTNLTRPVDIR
VVAAAKVDLGDPAARGDFREDLYYRLNVVTLSIPPLRERRDDIPLLFSHFLARASERFGREVPAISAAMR
AYLATHSWPGNVRELSHFAERVALGVEGNLGVPAAAPASSGATLPERLERYEADILKQALTAHCGDVKET
LQALGIPRKTFYDKLQRHGINRADYVERAGPGRPNAISKT

SEQ ID NO:11 promoter pDctA The DctD operator sites
(SEQ ID NOS:37 and 38) on promoter pDctA are underlined.

CTGCAGGAAGTTTGACCATGCGA<u>ACTGGTGCATCTTTTCGGCCAGG</u>ACGCCAGCACTT<u>CTGTGCGGAAAT
CCGCAC</u>ATATCCACGAACGGCAAGCGA

SEQ ID NO:12 Amino acid sequence of the $\sigma^{54}$ of *Pseudomonas putida*

MKPSLVLKMG QQLTMTPQLQ QAIRLLQLST LDLQQEIQEA LESNPMLERQ EDGEDFDNSD
PMADNAENKP AAEVQDNSFQ ESTVSADNLE DGEWSERIPN ELPVDTAWED IYQTSASSLP
SNDDDEWDFT TRTSAGESLQ SHLLWQLNLA PMSDTDRLIA VTLIDSINGQ GYLEDTLEEI
SAGFDPELDI ELDEVEAVLH RIQQFEPAGV GARNLGECLL LQLRQLPATT PWMTEAKRLV
TDFIDLLGSR DYSQLMRRMK IKEDELRQVI ELVQSLNPRP GSQIESSEPE YVVPDVIVRK
DSDRWLVELN QEAIPRLRVN PQYAGFVRRA DTSADNTFMR NQLQEARWFI KSLQSRNETL
MKVATRIVEH QRGFLDHGDE AMKPLVLHDI AEAVGMHEST ISRVTTQKYM HTPRGIYELK
YFFSSHVSTS EGGECSSTAI RAIIKKLVAA ENQKKPLSDS KIAGLLEAQG IQVARRTVAK
YRESLGIAPS SERKRLM

SEQ ID NO:13 Amino acid sequence of the $\sigma^{54}$ of *Pseudomonas aeruginosa*

MKPSLVLKMG QQLTMTPQLQ QAIRLLQLST LDLQQEIQEA LESNPMLERQ EDGDDFDNSD
PLADGAEQAA SAPQESPLQE SATPSVESLD DDQWSERIPS ELPVDTAWED IYQTSASSLP
SNDDDEWDFT ARTSSGESLH SHLLWQVNLA PMSDTDRMIA VTIIDSINND GYLEESLEEI

-continued

LAAIDPELDV ELDEVEVVLR RIQQLEPAGI GARNLRECLL LQLRQLPSTT PWLNEALRLV

SDYLDLLGGR DYSQLMRRMK LKEDELRQVI ELIQCLHPRP GSQIESSEAE YIVPDVIVRK

DNERWLVELN QEAMPRLRVN ATYAGMVRRA DSSADNTFMR NQLQEARWFI KTLQSRNETL

MKVATQIVEH QRGFLDYGEE AMKPLVLHDI AEAVGMHEST ISRVTTQKYM HTPRGIFELK

YFFSSHVSTA EGGECSSTAI RAIIKKLVAA ENAKKPLSDS KIAGLLEAQG IQVARRTVAK

YRESLGIAPS SERKRLV

SEQ ID NO:14. amino acid sequence of the $\sigma^{54}$ of *Vibrio fischeri* ES114

MKASLQLKMG QQLAMTPQLQ QAIRLLQLST LDLQQEIQEA LDSNPLLDVE EEALSTPETL

TSPEPKSEKE TASAEQETPI TDSSDVIESN NISEELEMDA SWDDVYSANS GSTGLAIDDD

TPIYQGETTE SLQDYLMWQA DLTPFTDLDR TIATTIIESL DEYGYLTSSL DDILESIGDE

EVEMDEVEAV LKRIQQFDPL GVASRDLAEC LLLQLATYPA NTPWLPETKL ILKDHINLLG

NRDYRQLAKE TKLKESDLKQ VMMLIHELDP RPGNRVIDTE TEYVIPDVSV FKHNGKWVVT

INPDSVPRLK VNAEYAALGK TMGNTPDGQF IRTNLQEAKW LIKSLESRNE TLLKVARCIV

EHQQDFFEYG EEAMKPMVLN DIALDVDMHE STISRVTTQK FMHTPRGIFE LKYFFSSHVS

TDNGGECSST AIRALVKKLV AAENQAKPLS DSKIATLLAE QGIQVARRTI AKYRESLGIA

PSNQRKRLL

SEQ ID NO:15 amino acid sequence of the $\sigma^{54}$ of *Escherichia coli* K12

MKQGLQLRLS QQLAMTPQLQ QAIRLLQLST LELQQELQQA LESNPLLEQI DTHEEIDTRE

TQDSETLDTA DALEQKEMPE ELPLDASWDT IYTAGTPSGT SGDYIDDELP VYQGETTQTL

QDYLMWQVEL TPFSDTDRAI ATSIVDAVDE TGYLTVPLED ILESIGDEEI DIDEVEAVLK

RIQRFDPVGV AAKDLRDCLL IQLSQFDKTT PWLEEARLII SDHLDLLANH DFRTLMRVTR

LKEDVLKEAV NLIQSLDPRP GQSIQTGEPE YVIPDVLVRK HNGHWTVELN SDSIPRLQIN

QHYASMCNNA RNDGDSQFIR SNLQDAKWLI KSLESRNDTL LRVSRCIVEQ QQAFFEQGEE

YMKPMVLADI AQAVEMHEST ISRVTTQKYL HSPRGIFELK YFFSSHVNTE GGGEASSTAI

RALVKKLIAA ENPAKPLSDS KLTSLLSEQG IMVARRTVAK YRESLSIPPS NQRKQLV

SEQ ID NO:16 PcaR promoter ($P_{PcaR}$): The transcription start site is in bold italics; PcaR operator sequence (SEQ ID NO:31) is underlined. This PcaR promoter sequence was used in Example 5.

GGCGGTCAATTGCGATTATCGGC<u>GTTTGTTCGATAATCGCACGA</u>*A*CCG

TTTG

SEQ ID NO:17 PcaIJ promoter ($P_{PcaIJ}$) The transcription start site is in bold italics; PcaR operator sequences (SEQ ID NOS:32 and 30) are underlined. This PcaIJ promoter sequence was used in Example 5.

TCCAGAACT<u>GCTCGCAGATCGCACAAC</u><u>AGTTCGATAATCGCAC</u>AAA*T*C

AGCC

What is claimed is:

1. A method of detecting a dicarboxylic acid, the method comprising
providing a recombinant host cell that comprises:
   a heterologous nucleic acid that encodes a transcription factor that comprises a binding region that can bind to and activate a promoter and a protein moiety that binds a dicarboxylic acid; and
   a heterologous nucleic acid that comprises a reporter gene operably linked to the promoter that is activated by the transcription factor;
culturing the host cell under conditions in which the transcription factor is produced, wherein the dicarboxylic acid, when present, binds to the protein, thereby activating the transcription factor to activate transcription of the reporter gene; and
detecting expression of the reporter gene.

2. The method of claim 1, wherein the dicarboxylic acid is a C4, C5, C6, or C7 dicarboxylic acid.

3. The method of claim 1, wherein the dicarboxylic acid is a C8, C9, C10, C11, C12, C13, or C14 dicarboxylic acid.

4. The method of claim 1, wherein the transcription factor is a PcaR transcription factor.

5. The method of claim 4, wherein the promoter is a PcaR promoter or a PcaIJ promoter.

6. The method of claim 1, wherein the recombinant host cell is an *Escherichia coli* cell.

* * * * *

SEQUENCE LISTING

<160> NUMBER OF SEQ ID NOS: 46

<210> SEQ ID NO 1
<211> LENGTH: 543
<212> TYPE: PRT
<213> ORGANISM: Escherichia coli
<220> FEATURE:
<223> OTHER INFORMATION: wild-type DcuS dicarboxylic acid binding
      protein, histidine kinase sensory polypeptide, reference sequence

<400> SEQUENCE: 1

```
Met Arg His Ser Leu Pro Tyr Arg Met Leu Arg Lys Arg Pro Met Lys
 1               5                  10                  15

Leu Ser Thr Thr Val Ile Leu Met Val Ser Ala Val Leu Phe Ser Val
            20                  25                  30

Leu Leu Val Val His Leu Ile Tyr Phe Ser Gln Ile Ser Asp Met Thr
        35                  40                  45

Arg Asp Gly Leu Ala Asn Lys Ala Leu Ala Val Ala Arg Thr Leu Ala
    50                  55                  60

Asp Ser Pro Glu Ile Arg Gln Gly Leu Gln Lys Lys Pro Gln Glu Ser
65                  70                  75                  80

Gly Ile Gln Ala Ile Ala Glu Ala Val Arg Lys Arg Asn Asp Leu Leu
                85                  90                  95

Phe Ile Val Val Thr Asp Met Gln Ser Leu Arg Tyr Ser His Pro Glu
            100                 105                 110

Ala Gln Arg Ile Gly Gln Pro Phe Lys Gly Asp Asp Ile Leu Lys Ala
        115                 120                 125

Leu Asn Gly Glu Glu Asn Val Ala Ile Asn Arg Gly Phe Leu Ala Gln
    130                 135                 140

Ala Leu Arg Val Phe Thr Pro Ile Tyr Asp Glu Asn His Lys Gln Ile
145                 150                 155                 160

Gly Val Val Ala Ile Gly Leu Glu Leu Ser Arg Val Thr Gln Gln Ile
                165                 170                 175

Asn Asp Ser Arg Trp Ser Ile Ile Trp Ser Val Leu Phe Gly Met Leu
            180                 185                 190

Val Gly Leu Ile Gly Thr Cys Ile Leu Val Lys Val Leu Lys Lys Ile
        195                 200                 205

Leu Phe Gly Leu Glu Pro Tyr Glu Ile Ser Thr Leu Phe Glu Gln Arg
    210                 215                 220

Gln Ala Met Leu Gln Ser Ile Lys Glu Gly Val Val Ala Val Asp Asp
225                 230                 235                 240

Arg Gly Glu Val Thr Leu Ile Asn Asp Ala Ala Gln Glu Leu Leu Asn
                245                 250                 255

Tyr Arg Lys Ser Gln Asp Glu Lys Leu Ser Thr Leu Ser His Ser
            260                 265                 270

Trp Ser Gln Val Val Asp Val Ser Glu Val Leu Arg Asp Gly Thr Pro
        275                 280                 285

Arg Arg Asp Glu Glu Ile Thr Ile Lys Asp Arg Leu Leu Leu Ile Asn
    290                 295                 300

Thr Val Pro Val Arg Ser Asn Gly Val Ile Ile Gly Ala Ile Ser Thr
305                 310                 315                 320

Phe Arg Asp Lys Thr Glu Val Arg Lys Leu Met Gln Arg Leu Asp Gly
                325                 330                 335

Leu Val Asn Tyr Ala Asp Ala Leu Arg Glu Arg Ser His Glu Phe Met
            340                 345                 350
```

```
Asn Lys Leu His Val Ile Leu Gly Leu Leu His Leu Lys Ser Tyr Lys
            355                 360                 365

Gln Leu Glu Asp Tyr Ile Leu Lys Thr Ala Asn Asn Tyr Gln Glu Glu
        370                 375                 380

Ile Gly Ser Leu Leu Gly Lys Ile Lys Ser Pro Val Ile Ala Gly Phe
385                 390                 395                 400

Leu Ile Ser Lys Ile Asn Arg Ala Thr Asp Leu Gly His Thr Leu Ile
                405                 410                 415

Leu Asn Ser Glu Ser Gln Leu Pro Asp Ser Gly Ser Glu Asp Gln Val
            420                 425                 430

Ala Thr Leu Ile Thr Thr Leu Gly Asn Leu Ile Glu Asn Ala Leu Glu
        435                 440                 445

Ala Leu Gly Pro Glu Pro Gly Gly Glu Ile Ser Val Thr Leu His Tyr
    450                 455                 460

Arg His Gly Trp Leu His Cys Glu Val Asn Asp Asp Gly Pro Gly Ile
465                 470                 475                 480

Ala Pro Asp Lys Ile Asp His Ile Phe Asp Lys Gly Val Ser Thr Lys
                485                 490                 495

Gly Ser Glu Arg Gly Val Gly Leu Ala Leu Val Lys Gln Gln Val Glu
            500                 505                 510

Asn Leu Gly Gly Ser Ile Ala Val Glu Ser Glu Pro Gly Ile Phe Thr
        515                 520                 525

Gln Phe Phe Val Gln Ile Pro Trp Asp Gly Glu Arg Ser Asn Arg
    530                 535                 540

<210> SEQ ID NO 2
<211> LENGTH: 239
<212> TYPE: PRT
<213> ORGANISM: Escherichia coli
<220> FEATURE:
<223> OTHER INFORMATION: wild-type DcuR transcription factor, reference
      sequence

<400> SEQUENCE: 2

Met Ile Asn Val Leu Ile Ile Asp Asp Ala Met Val Ala Glu Leu
  1               5                  10                  15

Asn Arg Arg Tyr Val Ala Gln Ile Pro Gly Phe Gln Cys Cys Gly Thr
            20                  25                  30

Ala Ser Thr Leu Glu Lys Ala Lys Glu Ile Ile Phe Asn Ser Asp Thr
        35                  40                  45

Pro Ile Asp Leu Ile Leu Leu Asp Ile Tyr Met Gln Lys Glu Asn Gly
    50                  55                  60

Leu Asp Leu Leu Pro Val Leu His Asn Ala Arg Cys Lys Ser Asp Val
65                  70                  75                  80

Ile Val Ile Ser Ser Ala Ala Asp Ala Ala Thr Ile Lys Asp Ser Leu
                85                  90                  95

His Tyr Gly Val Val Asp Tyr Leu Ile Lys Pro Phe Gln Ala Ser Arg
            100                 105                 110

Phe Glu Glu Ala Leu Thr Gly Trp Arg Gln Lys Lys Met Ala Leu Glu
        115                 120                 125

Lys His Gln Tyr Tyr Asp Gln Ala Glu Leu Asp Gln Leu Ile His Gly
    130                 135                 140

Ser Ser Ser Asn Glu Gln Asp Pro Arg Arg Leu Pro Lys Gly Leu Thr
145                 150                 155                 160

Pro Gln Thr Leu Arg Thr Leu Cys Gln Trp Ile Asp Ala His Gln Asp
                165                 170                 175
```

Tyr Glu Phe Ser Thr Asp Glu Leu Ala Asn Glu Val Asn Ile Ser Arg
            180                 185                 190

Val Ser Cys Arg Lys Tyr Leu Ile Trp Leu Val Asn Cys His Ile Leu
        195                 200                 205

Phe Thr Ser Ile His Tyr Gly Val Thr Gly Arg Pro Val Tyr Arg Tyr
    210                 215                 220

Arg Ile Gln Ala Glu His Tyr Ser Leu Leu Lys Gln Tyr Cys Gln
225                 230                 235

```
<210> SEQ ID NO 3
<211> LENGTH: 423
<212> TYPE: DNA
<213> ORGANISM: Escherichia coli
<220> FEATURE:
<221> NAME/KEY: promoter
<222> LOCATION: (1)...(423)
<223> OTHER INFORMATION: DcuB promoter and untranslated sequence (pDcuB)

<400> SEQUENCE: 3
gtgtttttaa tttcaaaacg ctaacaaaag ttaattaact attatgtcac ccgcattatg      60
tgtattttta cccacaaatg ggtagatcag attaatctat aaacctaatg acatctgccc     120
tgagaacaaa aaatagaccg ataaatatca ataagataac agcaaacaaa acattaacat     180
ctgcgcagta caaactataa acccatcgcc agagagtctt tctctctgaa aaagccgctt     240
atcacagtgc ataaatttgc cgctgcttta atcagccaat attcactgtg aggtatttgc     300
taaagccggt aacgaccaaa cggatattta gtcaggctct gaaacagtt catcaaaac      360 agaacgtgac tgtgatctat tcagcaaaaa tttaataggg attatcgcga gggttcacac     420
atg                                                                 423

<210> SEQ ID NO 4
<211> LENGTH: 178
<212> TYPE: DNA
<213> ORGANISM: Escherichia coli
<220> FEATURE:
<221> NAME/KEY: promoter
<222> LOCATION: (1)...(178)
<223> OTHER INFORMATION: DctA promoter (pDctA)

<400> SEQUENCE: 4
aaactgatta caaaacttta aaaagtgctg gtttgtgcga gccagctcaa acttttaac      60 cttttttgttt caattatgat ccaggtacat ttctgtgatg ttgtctgggt gttattttaa    120
ggccgcaggt accccataac cttacaagac ctgtggtttt actaaggac accctatg      178

<210> SEQ ID NO 5
<211> LENGTH: 212
<212> TYPE: DNA
<213> ORGANISM: Escherichia coli
<220> FEATURE:
<221> NAME/KEY: promoter
<222> LOCATION: (1)...(212)
<223> OTHER INFORMATION: FrdA promoter (pFrdA)

<400> SEQUENCE: 5
atggtttagt aattaaatta atcatcttca gtgataattt agccctcttg cgcactaaaa     60
aaatcgatct cgtcaaattt cagacttatc catcagacta tactgttgta cctataaagg    120
agcagtggaa tagcgttcgc agaccgtaac tttcaggtac ttaccctgaa gtacgtggct    180
gtgggataaa acaatctgg aggaatgtcg tg                                   212
```

```
<210> SEQ ID NO 6
<211> LENGTH: 291
<212> TYPE: PRT
<213> ORGANISM: Pseudomonas putida
<220> FEATURE:
<223> OTHER INFORMATION: transcription factor PcaR, reference sequence
<221> NAME/KEY: DOMAIN
<222> LOCATION: (47)...(98)
<223> OTHER INFORMATION: helix-turn-helix domain
<221> NAME/KEY: DOMAIN
<222> LOCATION: (160)...(288)
<223> OTHER INFORMATION: IclR family transcription regulator
      recognition domain

<400> SEQUENCE: 6

Met Ser Asp Glu Thr Pro Ala Asn Glu Ser Ala Asn Pro Glu Ser Ala
1               5                   10                  15

Arg Pro Ala Ala Pro Ala Leu Ala Pro Pro Ile Val Ala Ser Pro Ala
            20                  25                  30

Lys Arg Ile Gln Ala Phe Thr Gly Asp Pro Asp Phe Met Thr Ser Leu
        35                  40                  45

Ala Arg Gly Leu Ala Val Ile Gln Ala Phe Gln Glu Arg Lys Arg His
    50                  55                  60

Leu Thr Ile Ala Gln Ile Ser His Arg Thr Glu Ile Pro Arg Ala Ala
65                  70                  75                  80

Val Arg Arg Cys Leu His Thr Leu Ile Lys Leu Gly Tyr Ala Thr Thr
                85                  90                  95

Asp Gly Arg Thr Tyr Ser Leu Leu Pro Lys Val Leu Thr Leu Gly His
            100                 105                 110

Ala Tyr Leu Ser Ser Thr Pro Leu Ala Ile Ser Ala Gln Pro Tyr Leu
        115                 120                 125

Asp Arg Ile Ser Asp Gln Leu His Glu Ala Ala Asn Met Ala Thr Leu
    130                 135                 140

Glu Gly Asp Asp Ile Leu Tyr Ile Ala Arg Ser Ala Thr Val Glu Arg
145                 150                 155                 160

Leu Ile Ser Val Asp Leu Ser Val Gly Gly Arg Leu Pro Ala Tyr Cys
                165                 170                 175

Thr Ser Met Gly Arg Ile Leu Leu Ala Ala Met Asp Asp Thr Ser Leu
            180                 185                 190

Arg Glu Tyr Leu Asp Arg Ala Asp Leu Lys Ala Arg Thr Ser Arg Thr
        195                 200                 205

Leu Asn Asp Ala Glu Ser Leu Phe Ala Cys Ile Gln Gln Val Arg Ala
    210                 215                 220

Gln Gly Trp Cys Val Val Asp Gln Glu Leu Glu Gln Gly Leu Arg Ser
225                 230                 235                 240

Ile Ala Val Pro Ile Tyr Asp Ala Ser Gly Val Leu Ala Ala Leu
                245                 250                 255

Asn Val Ser Thr His Val Gly Arg Val Thr Arg Ser Glu Leu Glu Gln
            260                 265                 270

Arg Phe Leu Pro Ile Leu Leu Ala Ala Ser Arg Asp Leu Cys His Gln
        275                 280                 285

Leu Phe Gly
    290

<210> SEQ ID NO 7
<211> LENGTH: 53
<212> TYPE: DNA
<213> ORGANISM: Pseudomonas putida
<220> FEATURE:
<221> NAME/KEY: promoter
```

```
<222> LOCATION: (1)...(53)
<223> OTHER INFORMATION: PcaR promoter (pPcaR)

<400> SEQUENCE: 7
agcggtcaat tgcgattatc ggccgtttgt tcgataatcg cacgaacggg cgt         53

<210> SEQ ID NO 8
<211> LENGTH: 53
<212> TYPE: DNA
<213> ORGANISM: Pseudomonas putida
<220> FEATURE:
<221> NAME/KEY: promoter
<222> LOCATION: (1)...(53)
<223> OTHER INFORMATION: PcaIJ promoter (pPcaIJ)

<400> SEQUENCE: 8
accagaactg ctcgcacatc gcacaacagt tcgataatcg cacaaattcc gct         53

<210> SEQ ID NO 9
<211> LENGTH: 621
<212> TYPE: PRT
<213> ORGANISM: Sinorhizobium meliloti
<220> FEATURE:
<223> OTHER INFORMATION: DctB dicarboxylic acid binding polypeptide,
      histidine kinase, reference sequence

<400> SEQUENCE: 9
```

Met His His Val Arg Met Val Lys Leu Pro Ala Glu Ala Ser Asp Pro
 1               5                   10                  15

His Ala Leu Arg Ser Arg Ala Arg Arg Ser Trp Leu Val Phe Ala Ala
            20                  25                  30

Val Ala Leu Val Leu Leu Ala Ala Gly Leu Leu Leu Ala Arg Asp Tyr
        35                  40                  45

Gly Arg Ser Gln Ala Leu Ala Gly Leu Ala Gly Gln Ser Arg Ile Asp
    50                  55                  60

Ala Ser Leu Lys Ala Ser Leu Leu Arg Ala Val Val Glu Arg Gln Arg
65                  70                  75                  80

Ala Leu Pro Leu Val Leu Ala Asp Asp Ala Ala Ile Arg Gly Ala Leu
                85                  90                  95

Leu Ser Pro Asp Arg Pro Ser Leu Asp Arg Ile Asn Arg Lys Leu Glu
            100                 105                 110

Ala Leu Ala Thr Ser Ala Glu Ala Ala Val Ile Tyr Leu Ile Asp Arg
        115                 120                 125

Ser Gly Val Ala Val Ala Ala Ser Asn Trp Gln Glu Pro Thr Ser Phe
    130                 135                 140

Val Gly Asn Asp Tyr Ala Phe Arg Asp Tyr Phe Arg Leu Ala Val Arg
145                 150                 155                 160

Asp Gly Met Ala Glu His Phe Ala Met Gly Thr Val Ser Asn Arg Pro
                165                 170                 175

Gly Leu Tyr Ile Ser Arg Arg Val Asp Gly Pro Gly Pro Leu Gly
            180                 185                 190

Val Ile Val Ala Lys Leu Glu Phe Asp Gly Val Glu Ala Asp Trp Gln
        195                 200                 205

Ala Ser Gly Lys Pro Ala Tyr Val Thr Asp Arg Arg Gly Ile Val Leu
    210                 215                 220

Ile Thr Ser Leu Pro Ser Trp Arg Phe Met Thr Thr Lys Pro Ile Ala
225                 230                 235                 240

Glu Asp Arg Leu Ala Pro Ile Arg Glu Ser Leu Gln Phe Gly Asp Ala
                245                 250                 255

```
Pro Leu Leu Pro Leu Pro Phe Arg Lys Ile Glu Ala Arg Pro Asp Gly
            260                 265                 270

Ser Ser Thr Leu Asp Ala Leu Leu Pro Gly Asp Ser Thr Ala Ala Phe
        275                 280                 285

Leu Arg Val Glu Thr Met Val Pro Ser Thr Asn Trp Arg Leu Glu Gln
    290                 295                 300

Leu Ser Pro Leu Lys Ala Pro Leu Ala Ala Gly Ala Arg Glu Ala Gln
305                 310                 315                 320

Leu Leu Thr Leu Ala Ala Leu Val Pro Leu Leu Ala Leu Ala Ala Leu
                325                 330                 335

Leu Leu Arg Arg Arg Gln Val Val Ala Met Arg Ser Ala Glu Glu Arg
            340                 345                 350

Leu Ala Arg Asn Ala Leu Glu Ala Ser Val Glu Glu Arg Thr Arg Asp
        355                 360                 365

Leu Arg Met Ala Arg Asp Arg Leu Glu Thr Glu Ile Ala Asp His Arg
    370                 375                 380

Gln Thr Thr Glu Lys Leu Gln Ala Val Gln Gln Asp Leu Val Gln Ala
385                 390                 395                 400

Asn Arg Leu Ala Ile Leu Gly Gln Val Ala Ala Gly Val Ala His Glu
                405                 410                 415

Ile Asn Gln Pro Val Ala Thr Ile Arg Ala Tyr Ala Asp Asn Ala Arg
            420                 425                 430

Thr Phe Leu His Arg Gly Gln Thr Val Thr Ala Glu Asn Met Glu
        435                 440                 445

Ser Ile Ala Glu Leu Thr Glu Arg Val Gly Ala Ile Thr Asp Glu Leu
    450                 455                 460

Arg Arg Phe Ala Arg Lys Gly His Phe Ala Ala Gly Pro Thr Ala Met
465                 470                 475                 480

Lys Glu Val Val Glu Gly Ala Leu Met Leu Leu Arg Ser Arg Phe Ala
                485                 490                 495

Gly Arg Met Asp Ala Ile Arg Leu Asp Leu Pro Pro Asp Gly Leu Gln
            500                 505                 510

Ala Leu Gly Asn Arg Ile Arg Leu Glu Gln Val Leu Ile Asn Leu Leu
        515                 520                 525

Gln Asn Ala Leu Glu Ala Ile Gly Asp Ser Glu Asp Gly Ala Ile Gln
    530                 535                 540

Val Arg Cys Glu Glu Ala Ala Gly Gly Ile Ala Leu Thr Val Ala Asp
545                 550                 555                 560

Asn Gly Pro Gly Ile Ala Ala Asp Val Arg Glu Glu Leu Phe Thr Pro
                565                 570                 575

Phe Asn Thr Ser Lys Glu Asp Gly Leu Gly Leu Gly Leu Ala Ile Ser
            580                 585                 590

Lys Glu Ile Val Ser Asp Tyr Gly Gly Thr Ile Glu Val Glu Ser Gly
        595                 600                 605

Pro Ser Gly Thr Thr Phe Ala Val Asn Leu Lys Lys Ala
    610                 615                 620

<210> SEQ ID NO 10
<211> LENGTH: 460
<212> TYPE: PRT
<213> ORGANISM: Sinorhizobium meliloti
<220> FEATURE:
<223> OTHER INFORMATION: DctD transcription factor

<400> SEQUENCE: 10

Met Ser Ala Ala Pro Ser Val Phe Leu Ile Asp Asp Arg Asp Leu
```

```
                1               5                  10                  15
        Arg Lys Ala Met Gln Gln Thr Leu Glu Leu Ala Gly Phe Thr Val Ser
                        20                  25                  30

Ser Phe Ala Ser Ala Thr Glu Ala Leu Ala Glu Leu Ser Ala Asp Phe
                        35                  40                  45

Ala Gly Ile Val Ile Ser Asp Ile Arg Met Pro Gly Met Asp Gly Leu
                50                  55                  60

Ala Leu Phe Gly Lys Val Leu Ala Leu Asp Pro Asp Leu Pro Met Ile
        65                  70                  75                  80

Leu Val Thr Gly His Gly Asp Ile Pro Met Ala Val Gln Ala Ile Gln
                                85                  90                  95

Asp Gly Ala Tyr Asp Phe Ile Ala Lys Pro Phe Ala Ala Asp Arg Leu
                        100                 105                 110

Val Gln Ser Ala Arg Arg Ala Glu Lys Arg Arg Leu Val Met Glu
                        115                 120                 125

Asn Arg Ser Leu Arg Arg Ala Ala Glu Ala Ala Ser Glu Gly Leu Pro
                        130                 135                 140

Leu Ile Gly Gln Thr Pro Ala Met Glu Arg Leu Arg Gln Thr Leu Lys
        145                 150                 155                 160

His Ile Ala Asp Thr Asp Val Asp Val Leu Val Ala Gly Glu Thr Gly
                                165                 170                 175

Ser Gly Lys Glu Val Val Ala Thr Leu Leu His Gln Trp Ser Arg Arg
                        180                 185                 190

Arg Thr Gly Asn Phe Val Ala Leu Asn Cys Gly Ala Leu Pro Glu Thr
                        195                 200                 205

Val Ile Glu Ser Glu Leu Phe Gly His Glu Pro Gly Ala Phe Thr Gly
                        210                 215                 220

Ala Val Lys Lys Arg Ile Gly Arg Ile Glu His Ala Ser Gly Gly Thr
        225                 230                 235                 240

Leu Phe Leu Asp Glu Ile Glu Ala Met Pro Pro Ala Thr Gln Val Lys
                        245                 250                 255

Met Leu Arg Val Leu Glu Ala Arg Glu Ile Thr Pro Leu Gly Thr Asn
                        260                 265                 270

Leu Thr Arg Pro Val Asp Ile Arg Val Val Ala Ala Lys Val Asp
                        275                 280                 285

Leu Gly Asp Pro Ala Ala Arg Gly Asp Phe Arg Glu Asp Leu Tyr Tyr
                        290                 295                 300

Arg Leu Asn Val Val Thr Leu Ser Ile Pro Pro Leu Arg Glu Arg Arg
        305                 310                 315                 320

Asp Asp Ile Pro Leu Leu Phe Ser His Phe Leu Ala Arg Ala Ser Glu
                        325                 330                 335

Arg Phe Gly Arg Glu Val Pro Ala Ile Ser Ala Ala Met Arg Ala Tyr
                        340                 345                 350

Leu Ala Thr His Ser Trp Pro Gly Asn Val Arg Glu Leu Ser His Phe
                        355                 360                 365

Ala Glu Arg Val Ala Leu Gly Val Gly Asn Leu Gly Val Pro Ala
                370                 375                 380

Ala Ala Pro Ala Ser Ser Gly Ala Thr Leu Pro Glu Arg Leu Glu Arg
        385                 390                 395                 400

Tyr Glu Ala Asp Ile Leu Lys Gln Ala Leu Thr Ala His Cys Gly Asp
                        405                 410                 415

Val Lys Glu Thr Leu Gln Ala Leu Gly Ile Pro Arg Lys Thr Phe Tyr
                        420                 425                 430
```

Asp Lys Leu Gln Arg His Gly Ile Asn Arg Ala Asp Tyr Val Glu Arg
        435                 440                 445

Ala Gly Pro Gly Arg Pro Asn Ala Ile Ser Lys Thr
    450                 455                 460

<210> SEQ ID NO 11
<211> LENGTH: 97
<212> TYPE: DNA
<213> ORGANISM: Escherichia coli
<220> FEATURE:
<221> NAME/KEY: promoter
<222> LOCATION: (1)...(97)
<223> OTHER INFORMATION: Escherichia coli strain K12 promoter pDctA, P-
      DctA promoter

<400> SEQUENCE: 11
ctgcaggaag tttgaccatg cgaactggtg catcttttcg gccaggacgc cagcacttct    60
gtgcggaaat ccgcacatat ccacgaacgg caagcga                             97

<210> SEQ ID NO 12
<211> LENGTH: 497
<212> TYPE: PRT
<213> ORGANISM: Pseudomonas putida
<220> FEATURE:
<223> OTHER INFORMATION: 54-sigma RNA polymerase subunit

<400> SEQUENCE: 12

Met Lys Pro Ser Leu Val Leu Lys Met Gly Gln Gln Leu Thr Met Thr
  1               5                  10                  15

Pro Gln Leu Gln Gln Ala Ile Arg Leu Leu Gln Leu Ser Thr Leu Asp
             20                  25                  30

Leu Gln Gln Glu Ile Gln Glu Ala Leu Glu Ser Asn Pro Met Leu Glu
         35                  40                  45

Arg Gln Glu Asp Gly Glu Asp Phe Asp Asn Ser Asp Pro Met Ala Asp
     50                  55                  60

Asn Ala Glu Asn Lys Pro Ala Ala Glu Val Gln Asp Asn Ser Phe Gln
 65                  70                  75                  80

Glu Ser Thr Val Ser Ala Asp Asn Leu Glu Asp Gly Glu Trp Ser Glu
                 85                  90                  95

Arg Ile Pro Asn Glu Leu Pro Val Asp Thr Ala Trp Glu Asp Ile Tyr
            100                 105                 110

Gln Thr Ser Ala Ser Ser Leu Pro Ser Asn Asp Asp Glu Trp Asp
        115                 120                 125

Phe Thr Thr Arg Thr Ser Ala Gly Glu Ser Leu Gln Ser His Leu Leu
    130                 135                 140

Trp Gln Leu Asn Leu Ala Pro Met Ser Asp Thr Asp Arg Leu Ile Ala
145                 150                 155                 160

Val Thr Leu Ile Asp Ser Ile Asn Gly Gln Gly Tyr Leu Glu Asp Thr
                165                 170                 175

Leu Glu Glu Ile Ser Ala Gly Phe Asp Pro Glu Leu Asp Ile Glu Leu
            180                 185                 190

Asp Glu Val Glu Ala Val Leu His Arg Ile Gln Gln Phe Glu Pro Ala
        195                 200                 205

Gly Val Gly Ala Arg Asn Leu Gly Glu Cys Leu Leu Leu Gln Leu Arg
    210                 215                 220

Gln Leu Pro Ala Thr Thr Pro Trp Met Thr Glu Ala Lys Arg Leu Val
225                 230                 235                 240

Thr Asp Phe Ile Asp Leu Leu Gly Ser Arg Asp Tyr Ser Gln Leu Met
                245                 250                 255

```
Arg Arg Met Lys Ile Lys Glu Asp Glu Leu Arg Gln Val Ile Glu Leu
            260                 265                 270
Val Gln Ser Leu Asn Pro Arg Pro Gly Ser Gln Ile Glu Ser Ser Glu
        275                 280                 285
Pro Glu Tyr Val Val Pro Asp Val Ile Val Arg Lys Asp Ser Asp Arg
    290                 295                 300
Trp Leu Val Glu Leu Asn Gln Glu Ala Ile Pro Arg Leu Arg Val Asn
305                 310                 315                 320
Pro Gln Tyr Ala Gly Phe Val Arg Arg Ala Asp Thr Ser Ala Asp Asn
            325                 330                 335
Thr Phe Met Arg Asn Gln Leu Gln Glu Ala Arg Trp Phe Ile Lys Ser
        340                 345                 350
Leu Gln Ser Arg Asn Glu Thr Leu Met Lys Val Ala Thr Arg Ile Val
    355                 360                 365
Glu His Gln Arg Gly Phe Leu Asp His Gly Asp Glu Ala Met Lys Pro
370                 375                 380
Leu Val Leu His Asp Ile Ala Glu Ala Val Gly Met His Glu Ser Thr
385                 390                 395                 400
Ile Ser Arg Val Thr Thr Gln Lys Tyr Met His Thr Pro Arg Gly Ile
            405                 410                 415
Tyr Glu Leu Lys Tyr Phe Phe Ser Ser His Val Ser Thr Ser Glu Gly
        420                 425                 430
Gly Glu Cys Ser Ser Thr Ala Ile Arg Ala Ile Ile Lys Lys Leu Val
    435                 440                 445
Ala Ala Glu Asn Gln Lys Lys Pro Leu Ser Asp Ser Lys Ile Ala Gly
450                 455                 460
Leu Leu Glu Ala Gln Gly Ile Gln Val Ala Arg Arg Thr Val Ala Lys
465                 470                 475                 480
Tyr Arg Glu Ser Leu Gly Ile Ala Pro Ser Ser Glu Arg Lys Arg Leu
            485                 490                 495
Met

<210> SEQ ID NO 13
<211> LENGTH: 497
<212> TYPE: PRT
<213> ORGANISM: Pseudomonas aeruginosa
<220> FEATURE:
<223> OTHER INFORMATION: 54-sigma RNA polymerase subunit

<400> SEQUENCE: 13

Met Lys Pro Ser Leu Val Leu Lys Met Gly Gln Gln Leu Thr Met Thr
1               5                   10                  15
Pro Gln Leu Gln Gln Ala Ile Arg Leu Leu Gln Leu Ser Thr Leu Asp
            20                  25                  30
Leu Gln Gln Glu Ile Gln Glu Ala Leu Glu Ser Asn Pro Met Leu Glu
        35                  40                  45
Arg Gln Glu Asp Gly Asp Asp Phe Asp Asn Ser Asp Pro Leu Ala Asp
    50                  55                  60
Gly Ala Glu Gln Ala Ala Ser Ala Pro Gln Glu Ser Pro Leu Gln Glu
65                  70                  75                  80
Ser Ala Thr Pro Ser Val Glu Ser Leu Asp Asp Gln Trp Ser Glu
            85                  90                  95
Arg Ile Pro Ser Glu Leu Pro Val Asp Thr Ala Trp Glu Asp Ile Tyr
        100                 105                 110
Gln Thr Ser Ala Ser Ser Leu Pro Ser Asn Asp Asp Asp Glu Trp Asp
```

```
                115                 120                 125
Phe Thr Ala Arg Thr Ser Ser Gly Glu Ser Leu His Ser His Leu Leu
130                 135                 140
Trp Gln Val Asn Leu Ala Pro Met Ser Asp Thr Asp Arg Met Ile Ala
145                 150                 155                 160
Val Thr Ile Ile Asp Ser Ile Asn Asn Asp Gly Tyr Leu Glu Glu Ser
                165                 170                 175
Leu Glu Glu Ile Leu Ala Ala Ile Asp Pro Glu Leu Asp Val Glu Leu
                180                 185                 190
Asp Glu Val Glu Val Val Leu Arg Arg Ile Gln Gln Leu Glu Pro Ala
                195                 200                 205
Gly Ile Gly Ala Arg Asn Leu Arg Glu Cys Leu Leu Leu Gln Leu Arg
                210                 215                 220
Gln Leu Pro Ser Thr Thr Pro Trp Leu Asn Glu Ala Leu Arg Leu Val
225                 230                 235                 240
Ser Asp Tyr Leu Asp Leu Leu Gly Gly Arg Asp Tyr Ser Gln Leu Met
                245                 250                 255
Arg Arg Met Lys Leu Lys Glu Asp Glu Leu Arg Gln Val Ile Glu Leu
                260                 265                 270
Ile Gln Cys Leu His Pro Arg Pro Gly Ser Gln Ile Glu Ser Ser Glu
                275                 280                 285
Ala Glu Tyr Ile Val Pro Asp Val Ile Val Arg Lys Asp Asn Glu Arg
                290                 295                 300
Trp Leu Val Glu Leu Asn Gln Glu Ala Met Pro Arg Leu Arg Val Asn
305                 310                 315                 320
Ala Thr Tyr Ala Gly Met Val Arg Arg Ala Asp Ser Ser Ala Asp Asn
                325                 330                 335
Thr Phe Met Arg Asn Gln Leu Gln Glu Ala Arg Trp Phe Ile Lys Thr
                340                 345                 350
Leu Gln Ser Arg Asn Glu Thr Leu Met Lys Val Ala Thr Gln Ile Val
                355                 360                 365
Glu His Gln Arg Gly Phe Leu Asp Tyr Gly Glu Glu Ala Met Lys Pro
                370                 375                 380
Leu Val Leu His Asp Ile Ala Glu Ala Val Gly Met His Glu Ser Thr
385                 390                 395                 400
Ile Ser Arg Val Thr Thr Gln Lys Tyr Met His Thr Pro Arg Gly Ile
                405                 410                 415
Phe Glu Leu Lys Tyr Phe Phe Ser Ser His Val Ser Thr Ala Glu Gly
                420                 425                 430
Gly Glu Cys Ser Ser Thr Ala Ile Arg Ala Ile Ile Lys Lys Leu Val
                435                 440                 445
Ala Ala Glu Asn Ala Lys Lys Pro Leu Ser Asp Ser Lys Ile Ala Gly
                450                 455                 460
Leu Leu Glu Ala Gln Gly Ile Gln Val Ala Arg Arg Thr Val Ala Lys
465                 470                 475                 480
Tyr Arg Glu Ser Leu Gly Ile Ala Pro Ser Ser Glu Arg Lys Arg Leu
                485                 490                 495
Val

<210> SEQ ID NO 14
<211> LENGTH: 489
<212> TYPE: PRT
<213> ORGANISM: Vibrio fischeri
<220> FEATURE:
<223> OTHER INFORMATION: Vibrio fischeri strain ES114 54-sigma RNA
``` polymerase subunit

<400> SEQUENCE: 14

```
Met Lys Ala Ser Leu Gln Leu Lys Met Gly Gln Gln Leu Ala Met Thr
 1               5                  10                  15

Pro Gln Leu Gln Gln Ala Ile Arg Leu Leu Gln Leu Ser Thr Leu Asp
            20                  25                  30

Leu Gln Gln Glu Ile Gln Glu Ala Leu Asp Ser Asn Pro Leu Leu Asp
        35                  40                  45

Val Glu Glu Glu Ala Leu Ser Thr Pro Glu Thr Leu Thr Ser Pro Glu
    50                  55                  60

Pro Lys Ser Glu Lys Glu Thr Ala Ser Ala Glu Gln Glu Thr Pro Ile
65                  70                  75                  80

Thr Asp Ser Ser Asp Val Ile Glu Ser Asn Asn Ile Ser Glu Glu Leu
                85                  90                  95

Glu Met Asp Ala Ser Trp Asp Val Tyr Ser Ala Asn Ser Gly Ser
            100                 105                 110

Thr Gly Leu Ala Ile Asp Asp Thr Pro Ile Tyr Gln Gly Glu Thr
        115                 120                 125

Thr Glu Ser Leu Gln Asp Tyr Leu Met Trp Gln Ala Asp Leu Thr Pro
    130                 135                 140

Phe Thr Asp Leu Asp Arg Thr Ile Ala Thr Thr Ile Glu Ser Leu
145                 150                 155                 160

Asp Glu Tyr Gly Tyr Leu Thr Ser Ser Leu Asp Asp Ile Leu Glu Ser
                165                 170                 175

Ile Gly Asp Glu Glu Val Glu Met Asp Glu Val Glu Ala Val Leu Lys
            180                 185                 190

Arg Ile Gln Gln Phe Asp Pro Leu Gly Val Ala Ser Arg Asp Leu Ala
        195                 200                 205

Glu Cys Leu Leu Leu Gln Leu Ala Thr Tyr Pro Ala Asn Thr Pro Trp
    210                 215                 220

Leu Pro Glu Thr Lys Leu Ile Leu Lys Asp His Ile Asn Leu Leu Gly
225                 230                 235                 240

Asn Arg Asp Tyr Arg Gln Leu Ala Lys Glu Thr Lys Leu Lys Glu Ser
                245                 250                 255

Asp Leu Lys Gln Val Met Met Leu Ile His Glu Leu Asp Pro Arg Pro
            260                 265                 270

Gly Asn Arg Val Ile Asp Thr Glu Thr Glu Tyr Val Ile Pro Asp Val
        275                 280                 285

Ser Val Phe Lys His Asn Gly Lys Trp Val Val Thr Ile Asn Pro Asp
    290                 295                 300

Ser Val Pro Arg Leu Lys Val Asn Ala Glu Tyr Ala Ala Leu Gly Lys
305                 310                 315                 320

Thr Met Gly Asn Thr Pro Asp Gly Gln Phe Ile Arg Thr Asn Leu Gln
                325                 330                 335

Glu Ala Lys Trp Leu Ile Lys Ser Leu Glu Ser Arg Asn Glu Thr Leu
            340                 345                 350

Leu Lys Val Ala Arg Cys Ile Val Glu His Gln Gln Asp Phe Phe Glu
        355                 360                 365

Tyr Gly Glu Glu Ala Met Lys Pro Met Val Leu Asn Asp Ile Ala Leu
    370                 375                 380

Asp Val Asp Met His Glu Ser Thr Ile Ser Arg Val Thr Thr Gln Lys
385                 390                 395                 400

Phe Met His Thr Pro Arg Gly Ile Phe Glu Leu Lys Tyr Phe Phe Ser
```

```
                    405                 410                 415
Ser His Val Ser Thr Asp Asn Gly Gly Glu Cys Ser Ser Thr Ala Ile
                420                 425                 430

Arg Ala Leu Val Lys Lys Leu Val Ala Ala Glu Asn Gln Ala Lys Pro
                435                 440                 445

Leu Ser Asp Ser Lys Ile Ala Thr Leu Leu Ala Glu Gln Gly Ile Gln
                450                 455                 460

Val Ala Arg Arg Thr Ile Ala Lys Tyr Arg Glu Ser Leu Gly Ile Ala
465                 470                 475                 480

Pro Ser Asn Gln Arg Lys Arg Leu Leu
                485

<210> SEQ ID NO 15
<211> LENGTH: 477
<212> TYPE: PRT
<213> ORGANISM: Escherichia coli
<220> FEATURE:
<223> OTHER INFORMATION: Escherichia coli strain K12 54-sigma RNA
      polymerase subunit

<400> SEQUENCE: 15

Met Lys Gln Gly Leu Gln Leu Arg Leu Ser Gln Gln Leu Ala Met Thr
1               5                   10                  15

Pro Gln Leu Gln Gln Ala Ile Arg Leu Leu Gln Leu Ser Thr Leu Glu
                20                  25                  30

Leu Gln Gln Glu Leu Gln Gln Ala Leu Glu Ser Asn Pro Leu Leu Glu
            35                  40                  45

Gln Ile Asp Thr His Glu Glu Ile Asp Thr Arg Glu Thr Gln Asp Ser
        50                  55                  60

Glu Thr Leu Asp Thr Ala Asp Ala Leu Gln Lys Glu Met Pro Glu
65                  70                  75                  80

Glu Leu Pro Leu Asp Ala Ser Trp Asp Thr Ile Tyr Thr Ala Gly Thr
                85                  90                  95

Pro Ser Gly Thr Ser Gly Asp Tyr Ile Asp Asp Glu Leu Pro Val Tyr
                100                 105                 110

Gln Gly Glu Thr Thr Gln Thr Leu Gln Asp Tyr Leu Met Trp Gln Val
            115                 120                 125

Glu Leu Thr Pro Phe Ser Asp Thr Asp Arg Ala Ile Ala Thr Ser Ile
        130                 135                 140

Val Asp Ala Val Asp Glu Thr Gly Tyr Leu Thr Val Pro Leu Glu Asp
145                 150                 155                 160

Ile Leu Glu Ser Ile Gly Asp Glu Glu Ile Asp Ile Asp Glu Val Glu
                165                 170                 175

Ala Val Leu Lys Arg Ile Gln Arg Phe Asp Pro Val Gly Val Ala Ala
                180                 185                 190

Lys Asp Leu Arg Asp Cys Leu Leu Ile Gln Leu Ser Gln Phe Asp Lys
            195                 200                 205

Thr Thr Pro Trp Leu Glu Glu Ala Arg Leu Ile Ile Ser Asp His Leu
        210                 215                 220

Asp Leu Leu Ala Asn His Asp Phe Arg Thr Leu Met Arg Val Thr Arg
225                 230                 235                 240

Leu Lys Glu Asp Val Leu Lys Glu Ala Val Asn Leu Ile Gln Ser Leu
                245                 250                 255

Asp Pro Arg Pro Gly Gln Ser Ile Gln Thr Gly Glu Pro Glu Tyr Val
                260                 265                 270

Ile Pro Asp Val Leu Val Arg Lys His Asn Gly His Trp Thr Val Glu
```

```
                    275                 280                 285
Leu Asn Ser Asp Ser Ile Pro Arg Leu Gln Ile Asn Gln His Tyr Ala
    290                 295                 300
Ser Met Cys Asn Asn Ala Arg Asn Asp Gly Asp Ser Gln Phe Ile Arg
305                 310                 315                 320
Ser Asn Leu Gln Asp Ala Lys Trp Leu Ile Lys Ser Leu Glu Ser Arg
                325                 330                 335
Asn Asp Thr Leu Leu Arg Val Ser Arg Cys Ile Val Glu Gln Gln Gln
            340                 345                 350
Ala Phe Phe Glu Gln Gly Glu Glu Tyr Met Lys Pro Met Val Leu Ala
        355                 360                 365
Asp Ile Ala Gln Ala Val Glu Met His Glu Ser Thr Ile Ser Arg Val
    370                 375                 380
Thr Thr Gln Lys Tyr Leu His Ser Pro Arg Gly Ile Phe Glu Leu Lys
385                 390                 395                 400
Tyr Phe Phe Ser Ser His Val Asn Thr Glu Gly Gly Gly Glu Ala Ser
                405                 410                 415
Ser Thr Ala Ile Arg Ala Leu Val Lys Lys Leu Ile Ala Ala Glu Asn
            420                 425                 430
Pro Ala Lys Pro Leu Ser Asp Ser Lys Leu Thr Ser Leu Leu Ser Glu
        435                 440                 445
Gln Gly Ile Met Val Ala Arg Arg Thr Val Ala Lys Tyr Arg Glu Ser
    450                 455                 460
Leu Ser Ile Pro Pro Ser Asn Gln Arg Lys Gln Leu Val
465                 470                 475

<210> SEQ ID NO 16
<211> LENGTH: 53
<212> TYPE: DNA
<213> ORGANISM: Pseudomonas putida
<220> FEATURE:
<221> NAME/KEY: promoter
<222> LOCATION: (1)...(53)
<223> OTHER INFORMATION: PcaR promoter (P-PcaR)

<400> SEQUENCE: 16
ggcggtcaat tgcgattatc ggccgtttgt tcgataatcg cacgaaccgt ttg          53

<210> SEQ ID NO 17
<211> LENGTH: 53
<212> TYPE: DNA
<213> ORGANISM: Pseudomonas putida
<220> FEATURE:
<221> NAME/KEY: promoter
<222> LOCATION: (1)...(53)
<223> OTHER INFORMATION: PcaIJ promoter (P-PcaIJ)

<400> SEQUENCE: 17
tccagaactg ctcgcagatc gcacaacagt tcgataatcg cacaaattca gcc          53

<210> SEQ ID NO 18
<211> LENGTH: 251
<212> TYPE: PRT
<213> ORGANISM: Sinorhizobium fredii
<220> FEATURE:
<223> OTHER INFORMATION: Sinorhizobium fredii strain NGR234 IclR family
      transcriptional regulator, NGR_b21400 locus

<400> SEQUENCE: 18

Met Arg Glu Thr Asp Phe Val Ser Gly Phe Ala Arg Gly Leu Lys Val
1               5                   10                  15
```

```
Ile Glu Ala Phe Gly Glu Ala Gln Pro Arg Leu Ser Ile Ala Glu Ala
            20                  25                  30

Ser Lys Ile Thr Gly Leu Asp Arg Ala Thr Val Arg Arg Ser Leu Leu
        35                  40                  45

Thr Leu Ser Glu Leu Gly Tyr Ala Asp Tyr Asp Gly Lys Phe Phe Thr
    50                  55                  60

Leu Thr Pro Arg Ile Leu Arg Leu Gly His Ala Tyr Leu Ser Ala Thr
65                  70                  75                  80

Pro Leu Pro Ala Ile Val Gln Pro Tyr Leu Asp Gln Leu Ser Glu Lys
                85                  90                  95

Ala Gly Gln Ser Ala Ser Ala Ser Val Leu Asp Gly Thr Glu Val Val
            100                 105                 110

Tyr Val Ala Arg Ala Ser Gln Arg Arg Val Met Ser Ile Asn Leu Met
        115                 120                 125

Pro Gly Ser Arg Leu Pro Ala Tyr Cys Ala Ser Met Gly Arg Val Leu
    130                 135                 140

Leu Ala Ala Leu Pro Glu Ala Glu Ala Arg Glu Ile Leu Gly Arg Thr
145                 150                 155                 160

Glu Leu Lys Ala Asn Thr Pro Arg Thr Lys Thr Asp Leu Glu Glu Leu
                165                 170                 175

Met Ala Glu Phe Arg Lys Val Arg Glu Leu Gly Tyr Ala Val Ile Asp
            180                 185                 190

Gln Glu Leu Glu Leu Gly Leu Cys Ser Ile Ala Val Pro Leu Met Asn
        195                 200                 205

Ala Arg Gly Gln Val Val Ala Ala Leu Asn Ile Gly Ala Pro Ala Ala
    210                 215                 220

His Val Ala Ala Ser Glu Leu Ala Glu Arg Tyr Leu Pro Leu Leu Lys
225                 230                 235                 240

Glu Thr Gln Ala Ala Leu Arg Pro Leu Val Gln
                245                 250
```

<210> SEQ ID NO 19
<211> LENGTH: 251
<212> TYPE: PRT
<213> ORGANISM: Brucella sp.
<220> FEATURE:
<223> OTHER INFORMATION: Brucella sp. strain BO2 beta-ketoadipate pathway transcriptional regulator, PcaR/PcaU/PobR family

<400> SEQUENCE: 19

```
Met Arg Glu Thr Asp Phe Val Gly Gly Phe Ala Lys Gly Leu Arg Val
 1               5                  10                  15

Ile Glu Ala Phe Gly Glu Asp Arg Pro Arg Leu Ser Ile Ala Asp Val
            20                  25                  30

Ser Lys Ile Thr Gly Leu Asp Arg Ala Thr Ala Arg Arg Cys Leu Leu
        35                  40                  45

Thr Leu Ala Glu Leu Gly Tyr Ala Glu Tyr Asp Gly Lys Phe Phe Met
    50                  55                  60

Leu Leu Pro Arg Ile Leu Arg Leu Gly His Ala Tyr Leu Ser Gly Thr
65                  70                  75                  80

Pro Leu Pro Thr Ile Ile Gln Pro His Leu Asp Arg Leu Ser Gln Ser
                85                  90                  95

Val Gly Glu Ser Ala Ser Ala Ser Val Leu Asp Gly Ala Glu Ile Val
            100                 105                 110

Tyr Ile Ala Arg Ala Ser Gln Met Arg Val Ile Ser Ile Asn Leu Met
        115                 120                 125
```

```
Ala Gly Ser Arg Leu Pro Ala Tyr Cys Ala Ser Met Gly Arg Val Leu
            130                 135                 140

Leu Ala Trp Leu Asp Glu Ser Glu Ala Arg Thr Ile Leu Glu Gln Thr
145                 150                 155                 160

Glu Leu Gln Ala Arg Thr Pro Phe Thr Gln Thr Asp Leu Glu Lys Leu
                165                 170                 175

Met Glu Glu Leu Arg Arg Ile Arg Ala Gln Gly Phe Ala Val Asn Asp
            180                 185                 190

Gln Glu Leu Glu Leu Gly Leu Arg Ser Ile Ala Val Pro Val Phe Asn
        195                 200                 205

His Arg Gly Ala Val Val Ala Ala Leu Asn Ile Gly Ala Pro Val Ala
    210                 215                 220

His Val Glu Val Ser Asp Leu Val Gly Arg Ile Leu Pro Glu Met Leu
225                 230                 235                 240

Lys Ile Gln Ser Glu Leu Arg Ser Met Leu Arg
                245                 250

<210> SEQ ID NO 20
<211> LENGTH: 280
<212> TYPE: PRT
<213> ORGANISM: Pseudomonas fluorescens
<220> FEATURE:
<223> OTHER INFORMATION: Pseudomonas fluorescens strain WH6 Pca regulon
      regulatory protein pcaR, PFWH6_1380 locus

<400> SEQUENCE: 20

Met Asn Asp Gln Leu Arg Asn Ser Phe Ala Ser Ala Ala Pro Pro Ile
1               5                   10                  15

Val Ala Ser Pro Ala Lys Arg Ile Gln Ala Phe Thr Gly Asp Pro Asp
            20                  25                  30

Phe Met Thr Ser Leu Ala Arg Gly Leu Ala Val Val Gln Ala Phe Gln
        35                  40                  45

Glu Arg Lys Arg His Leu Thr Ile Ala Gln Ile Ser His Arg Thr Glu
    50                  55                  60

Ile Pro Arg Ala Ala Val Arg Arg Cys Leu His Thr Leu Ile Lys Leu
65                  70                  75                  80

Gly Tyr Ala Thr Thr Asp Gly Arg Thr Tyr Ser Leu Leu Pro Lys Val
                85                  90                  95

Leu Thr Leu Gly His Ala Tyr Leu Ser Ser Thr Pro Leu Ala Val Ser
            100                 105                 110

Ala Gln Pro Tyr Leu Asp Arg Met Ser Glu Gln Leu His Glu Ala Cys
        115                 120                 125

Asn Met Ala Thr Leu Glu Gly Asp Asp Ile Leu Tyr Ile Ala Arg Ser
130                 135                 140

Ala Thr Thr Gln Arg Leu Ile Ser Val Asp Leu Ser Val Gly Gly Arg
145                 150                 155                 160

Leu Pro Ala Tyr Cys Thr Ser Met Gly Arg Ile Leu Ala Ala Leu
                165                 170                 175

Asp Asp Ala Ser Leu Gln Asp Tyr Leu Asp His Ala Asp Leu Gln Thr
            180                 185                 190

Lys Thr Ser Arg Thr Leu Thr Thr Pro Glu Ala Leu Phe Glu Cys Leu
        195                 200                 205

Gln Gln Val Arg Gln Gly Trp Cys Ile Val Asp Gln Glu Leu Glu
    210                 215                 220

Gln Gly Leu Arg Ser Ile Ala Val Pro Val Tyr Asp Ala Ser Gly Gln
225                 230                 235                 240
```

```
Val Leu Ala Ala Leu Asn Val Ser Thr His Ala Gly Arg Val Ser Arg
                245                 250                 255

Ser Glu Leu Glu Gln Arg Phe Leu Pro Ser Met Leu Ser Ala Ser Arg
            260                 265                 270

Glu Leu Ser Thr Gln Leu Phe Ala
            275                 280

<210> SEQ ID NO 21
<211> LENGTH: 280
<212> TYPE: PRT
<213> ORGANISM: Pseudomonas syringae
<220> FEATURE:
<223> OTHER INFORMATION: Pseudomonas syringae pathovar syringae strain
      B728a regulatory protein IclR, Psyr_4014 locus

<400> SEQUENCE: 21

Met Asn Asp Glu Leu Arg Lys Ser Phe Ala Ser Leu Ala Pro Pro Ile
1               5                   10                  15

Val Ala Ser Pro Ala Lys Arg Ile Gln Ala Leu Thr Gly Asp Pro Asp
            20                  25                  30

Phe Met Thr Ser Leu Ala Arg Gly Leu Ala Val Ile His Ala Phe Gln
        35                  40                  45

Glu Arg Lys Arg His Leu Thr Ile Ala Gln Ile Ser His Arg Thr Glu
    50                  55                  60

Ile Pro Arg Ala Ala Val Arg Arg Cys Leu Thr Leu Ile Lys Leu
65                  70                  75                  80

Gly Tyr Ala Thr Thr Asp Gly Arg Thr Tyr Ser Leu Leu Pro Lys Val
                85                  90                  95

Leu Thr Leu Gly His Ala Tyr Leu Ser Ser Thr Pro Leu Ala Thr Ser
            100                 105                 110

Ser Gln Pro Tyr Leu Asp Arg Met Ser Asp Gln Leu His Glu Ala Cys
        115                 120                 125

Asn Met Ala Thr Leu Glu Gly Asp Asp Ile Leu Tyr Ile Ala Arg Ser
    130                 135                 140

Ala Thr Thr Gln Arg Leu Ile Ser Val Asp Leu Ser Val Gly Gly Arg
145                 150                 155                 160

Leu Pro Ala Tyr Cys Thr Ser Met Gly Arg Ile Leu Leu Ala Ala Leu
                165                 170                 175

Asp Asp Val Ser Leu His Glu Tyr Leu Asp His Val Asp Leu Gln Pro
            180                 185                 190

Lys Thr Ser Arg Thr Ile Arg Thr Pro Glu Ala Leu Leu Glu Cys Leu
        195                 200                 205

Gln Leu Val Arg Gln Gln Gly Trp Cys Ile Val Asp Gln Glu Leu Glu
    210                 215                 220

Gln Gly Leu Arg Ser Ile Ala Val Pro Val Tyr Asp Ala Ser Gly Gln
225                 230                 235                 240

Val Leu Ala Ala Leu Asn Val Ser Thr Ser Ala Gly Arg Val Ala Arg
                245                 250                 255

Ser Glu Leu Glu Gln Arg Phe Leu Pro Ile Met Leu Asp Ala Ser Arg
            260                 265                 270

Asp Leu Ser Thr Gln Leu Phe Thr
        275                 280

<210> SEQ ID NO 22
<211> LENGTH: 279
<212> TYPE: PRT
<213> ORGANISM: Pseudomonas aeruginosa
<220> FEATURE:
```

-continued

<223> OTHER INFORMATION: Pseudomonas aeruginosa strain PAO1
      transcriptional regulator PcaR, PA0155 locus

<400> SEQUENCE: 22

Met Ser Glu Leu Pro Glu His Pro Ala Thr Leu Ala Pro Pro Thr Val
1               5                   10                  15

Leu Ser Pro Ala Lys Arg Ile Glu Ala Phe Thr Gly Asp Pro Asn Phe
            20                  25                  30

Met Thr Ser Leu Ala Arg Gly Leu Ala Val Ile His Ala Phe Gln Glu
        35                  40                  45

Arg Lys Arg His Leu Thr Ile Ala Gln Ile Ser His Arg Thr Glu Ile
    50                  55                  60

Pro Arg Ala Ala Val Arg Arg Cys Leu His Thr Leu Met Gln Leu Gly
65                  70                  75                  80

Tyr Ala Thr Thr Asp Gly Arg Thr Tyr Ser Leu Leu Pro Lys Val Leu
                85                  90                  95

Thr Leu Gly His Ala Tyr Leu Ser Ser Thr Pro Leu Ala Ile Thr Ala
            100                 105                 110

Gln Pro Ile Leu Asp Arg Leu Ser Glu Gln Leu His Glu Ala Cys Ser
        115                 120                 125

Met Ala Thr Leu Glu Gly Asp Asp Val Leu Tyr Ile Ala Arg Ser Ala
    130                 135                 140

Thr Pro Gln Arg Leu Ile Ser Val Asp Leu Asn Val Gly Ser Arg Leu
145                 150                 155                 160

Pro Ala Tyr Cys Thr Ser Met Gly Arg Ile Leu Leu Ala Ala Leu Asp
                165                 170                 175

Asp Asp Ala Leu His Ala Tyr Phe Gly Gly Val Glu Met Gln Ala Lys
            180                 185                 190

Thr Ser Arg Thr Leu Tyr Thr Pro Glu Thr Leu Leu Pro Cys Leu Val
        195                 200                 205

Glu Ile Arg Arg Gln Gly Trp Cys Ile Val Asp Gln Glu Leu Glu Val
    210                 215                 220

Gly Leu Arg Ser Leu Ala Val Pro Val Arg Asp Ser Ala Gly His Val
225                 230                 235                 240

Leu Ala Ala Leu Asn Val Gly Thr His Ala Gly Arg Val Ser Arg Ala
                245                 250                 255

Glu Leu Glu Ser Arg Phe Leu Pro Leu Leu Glu Ala Ser Arg Glu
            260                 265                 270

Leu Ser Ala Arg Leu Phe Thr
        275

<210> SEQ ID NO 23
<211> LENGTH: 282
<212> TYPE: PRT
<213> ORGANISM: Ralstonia eutropha
<220> FEATURE:
<223> OTHER INFORMATION: Ralstonia eutropha strain H16 IclR family
      transcriptional regulator, H16_B2545 locus

<400> SEQUENCE: 23

Met Asp Val Leu Arg Pro Leu Gly Leu Gly His Ala Gln Ala Asp Thr
1               5                   10                  15

Val Arg Val Ala Arg Pro Gln Ala Asp Leu Leu Ala Ser Phe Ala Gly
            20                  25                  30

Asp Pro Asn Phe Met Leu Ser Leu Ala Arg Gly Leu Thr Val Leu Glu
        35                  40                  45

Ala Phe Ser Glu Arg Lys Arg Pro Leu Thr Ile Ser Gln Val Ala Gln

```
                    50                  55                  60
Arg Thr Gln Leu Ser Arg Ala Ser Val Arg Arg Cys Leu Tyr Thr Leu
 65                  70                  75                  80

Glu Gln Leu Gly Tyr Val Ser Gln Gln Asp Gly Gln Phe Ala Leu Arg
                 85                  90                  95

Pro Arg Val Leu His Leu Gly His Ala Tyr Phe Ser Ser Thr Ser Leu
            100                 105                 110

Val Ser Leu Ala Gln Pro Ile Leu Asp Asn Leu Ser Ala Arg Ile His
            115                 120                 125

Glu Thr Cys Thr Leu Ala Ile Leu Asp Gly Thr Asp Ile Leu Tyr Leu
        130                 135                 140

Val Arg Ser Glu Val Gln Arg Val Leu Asn Tyr Ser Leu Gly Met Gly
145                 150                 155                 160

Ser Arg Leu Pro Ala Tyr Cys Thr Ser Asn Gly Arg Leu Leu Leu Ala
                165                 170                 175

His Gln Pro Ala Thr Val Leu Asp Gly Phe Phe Glu His Ala Glu Leu
            180                 185                 190

Arg Pro Arg Thr Leu Gln Thr Lys Val Ser Arg Gln Glu Leu Glu Ala
        195                 200                 205

Cys Phe Glu Arg Ala Arg Glu Val Asp Tyr Val Ile Val Asp Glu Glu
    210                 215                 220

Leu Glu Pro Gly Leu Arg Ala Met Ala Val Pro Val Arg Ser Ala Ser
225                 230                 235                 240

Gly Ile Val Leu Ala Gly Leu Ser Val Ser Val Arg Ala Ala Arg Val
                245                 250                 255

Ser Glu Thr Glu Met Ile Ser Arg Leu Leu Pro Pro Ile Arg Glu Ala
            260                 265                 270

Ala Ala Ala Ile Gly Arg Leu Ile Gly Ser
        275                 280

<210> SEQ ID NO 24
<211> LENGTH: 268
<212> TYPE: PRT
<213> ORGANISM: Citrobacter rodentium
<220> FEATURE:
<223> OTHER INFORMATION: Citrobacter rodentium strain ICC168 Pca regulon
      regulatory protein, pcaR, ROD_16691 locus

<400> SEQUENCE: 24

Met Glu Lys His Pro Asp Asp Arg Leu Asn Asn Glu Ala Asp Pro Phe
  1               5                  10                  15

Lys Gly Asp Pro Asn Phe Met Ala Ser Leu Ala Arg Gly Leu Glu Val
             20                  25                  30

Ile Gln Ala Phe Thr Pro Gln Arg Arg Val Leu Ser Ile Ser Gln Ile
         35                  40                  45

Ser Gln Lys Thr Gly Ile Pro Arg Ala Ala Val Arg Arg Cys Leu Tyr
     50                  55                  60

Thr Leu Ser Lys Leu Gly Phe Val Tyr Ala Gln Asp Gly Lys Asn Phe
 65                  70                  75                  80

Glu Leu Arg Pro Arg Ile Leu Ala Leu Gly His Ala Tyr Leu Ala Ser
                 85                  90                  95

Thr Pro Leu Ala Arg Ala Thr Gln Pro Val Leu Lys His Leu Ser Glu
            100                 105                 110

Met Leu Asn Glu Ser Cys Ser Ile Ala Thr Leu Asp Gly Asp Asp Ile
        115                 120                 125

Leu Tyr Ile Ala Arg Ala Ser Ser Ser Arg Ile Met Thr Ile Asp Leu
```

```
                    130                 135                 140
Asp Ile Gly Ser Arg Leu Pro Ala Trp Ser Thr Ser Met Gly Arg Val
145                 150                 155                 160

Leu Leu Ser His Leu Ser Glu Asp Lys Leu Asn Asp Met Leu Gly Arg
                    165                 170                 175

Ile Thr Met Ile Arg Tyr Thr Ser Gln Thr Val Ser Ser Val Ala Ala
                180                 185                 190

Leu Arg Ala Glu Leu Lys Lys Val Arg Gln Gln Gly Tyr Ala Leu Asn
            195                 200                 205

Asp Gln Glu Leu Glu Met Gly Leu Arg Ser Ile Ala Val Pro Leu Ala
210                 215                 220

Asn Ala Gln Gly Gln Val Gln Ala Ala Leu Asn Val Gly Val His Ala
225                 230                 235                 240

Gly Gln Val Thr Ala Glu Glu Leu Arg Thr Arg Val Leu Pro Glu Leu
                245                 250                 255

Gln Lys Ala Ala Gln Glu Leu Ser Leu Leu Asp
                260                 265
```

<210> SEQ ID NO 25
<211> LENGTH: 268
<212> TYPE: PRT
<213> ORGANISM: Escherichia fergusonii
<220> FEATURE:
<223> OTHER INFORMATION: Escherichia fergusonii strain ATCC 35469 Pca
      regulon regulatory protein, PcaR, EFER_1637 locus

<400> SEQUENCE: 25

```
Met Glu Lys His Pro Asp Asp Arg Leu Asn Ser Asp Ala Asp Pro Phe
1               5                   10                  15

Lys Gly Asp Pro Asn Phe Met Ala Ser Leu Ala Arg Gly Leu Asp Val
                20                  25                  30

Ile Gln Ala Phe Thr Pro Gln Arg Arg Met Met Ser Ile Ser Gln Ile
            35                  40                  45

Ser Gln Lys Thr Gly Ile Pro Arg Ala Ala Val Arg Arg Cys Leu Tyr
50                  55                  60

Thr Leu Gly Lys Leu Gly Phe Val Tyr Ala Gln Asp Gly Lys Asn Phe
65                  70                  75                  80

Glu Leu Arg Pro Arg Ile Leu Ala Leu Gly His Ala Tyr Leu Ala Ser
                85                  90                  95

Thr Pro Leu Ala Arg Ala Ala Gln Pro Val Leu Lys His Leu Ser Glu
            100                 105                 110

Met Leu Asn Glu Ser Cys Ser Ile Ala Thr Leu Asp Gly Asp Asp Ile
        115                 120                 125

Leu Tyr Ile Ala Arg Ala Ser Ser Ser Arg Ile Met Thr Ile Asp Leu
    130                 135                 140

Asp Ile Gly Ser Arg Leu Pro Ala Trp Ala Thr Ser Met Gly Arg Val
145                 150                 155                 160

Leu Leu Ser His Leu Pro Glu Glu Asn Leu Asn Asp Leu Leu Gly Arg
                165                 170                 175

Val Thr Met Ile Arg Tyr Thr Ser Gln Thr Val Asp Ser Val Ser Ala
                180                 185                 190

Leu Arg Glu Glu Leu Lys Lys Val Gln Gln Gly Tyr Ala Leu Asn
            195                 200                 205

Asp Gln Glu Leu Glu Met Gly Leu Arg Ser Ile Ala Val Pro Leu Ser
210                 215                 220

Asn Thr Arg Gly Gln Val Leu Ala Ala Leu Asn Val Gly Val His Ala
```

225                 230                 235                 240

Gly Gln Val Ser Ala Asp Glu Leu Leu Ser Arg Val Leu Pro Glu Leu
                245                 250                 255

Gln Lys Ala Ala Gln Glu Leu Ser Leu Leu Leu Asp
            260                 265

<210> SEQ ID NO 26
<211> LENGTH: 268
<212> TYPE: PRT
<213> ORGANISM: Klebsiella pneumoniae
<220> FEATURE:
<223> OTHER INFORMATION: Klebsiella pneumoniae strain 342 Pca regulon
      regulatory protein, pcaR, KPK_2918 locus

<400> SEQUENCE: 26

Met Asp Lys His Pro Asp Asp Leu Leu Thr Gly Asp Gly Asp Pro Phe
 1               5                  10                  15

Lys Gly Asp Pro Asn Phe Met Ala Ser Leu Ala Arg Gly Leu Glu Val
            20                  25                  30

Ile Gln Ala Phe Thr Pro Gln Arg Pro Leu Leu Ser Ile Ser Gln Ile
        35                  40                  45

Ser Gln Lys Thr Gly Ile Pro Arg Ala Ala Val Arg Arg Cys Leu Tyr
50                  55                  60

Thr Leu Ser Lys Leu Gly Phe Val Tyr Ala Glu Asp Gly Lys Asn Phe
65                  70                  75                  80

Gln Leu Arg Pro Arg Ile Leu Ala Leu Gly His Ala Trp Leu Ala Ser
                85                  90                  95

Thr Pro Leu Ala Arg Ser Ala Gln Pro Val Leu Arg His Leu Ser Glu
            100                 105                 110

Met Leu Asn Glu Ser Cys Ser Ile Ala Thr Leu Asp Gly Asp Asp Ile
        115                 120                 125

Leu Tyr Ile Ala Arg Ala Ser Ser Ser Arg Ile Met Thr Ile Asp Leu
130                 135                 140

Asp Ile Gly Ser Arg Leu Pro Ala Trp Ala Thr Ser Met Gly Arg Val
145                 150                 155                 160

Leu Leu Ser His Gln Pro Glu Glu Lys Leu Asn Asp Met Leu Ala Arg
                165                 170                 175

Val Thr Met Ile Arg Tyr Thr Pro Gln Thr Val Asp Ser Val Ala Lys
            180                 185                 190

Leu Arg Thr Glu Leu Lys Arg Val His Gln Gln Gly Tyr Ala Leu Asn
        195                 200                 205

Asp Gln Glu Leu Glu Met Gly Leu Arg Ser Leu Ala Val Pro Leu Phe
210                 215                 220

Asn Ala Gln Gly Gln Val Gln Ala Ala Leu Asn Val Gly Val His Ala
225                 230                 235                 240

Gly Gln Met Ser Ala Arg Glu Met Ile Asp Arg Val Leu Pro Glu Leu
                245                 250                 255

Gln Lys Ala Ala Arg Glu Leu Thr Leu Leu Leu Arg
            260                 265

<210> SEQ ID NO 27
<211> LENGTH: 258
<212> TYPE: PRT
<213> ORGANISM: Corynebacterium ammoniagenes
<220> FEATURE:
<223> OTHER INFORMATION: Corynebacterium ammoniagenes strain DSM 20306
      Pca regulon regulatory protein PcaR, HMPREF0281_01032 locus

<400> SEQUENCE: 27

```
Met Val Ser Pro Ser Ser Asp Phe Val Gln Ser Phe Ala Arg Gly Leu
  1               5                  10                  15

Met Val Ile Arg Ser Phe Asp Ala Thr Ala Pro Ser Gln Thr Leu Ser
             20                  25                  30

Gln Val Ala Ala Ala Thr Gly Leu Ser Arg Ala Ala Arg Arg Phe
         35                  40                  45

Leu His Thr Leu Val Glu Glu Gly Tyr Ala Val Asn Asn Asp Gly Gln
 50                  55                      60

Phe Ser Leu Thr Pro Arg Val Met Glu Leu Gly Tyr Ser Tyr Leu Ser
 65                  70                  75                  80

Ala Leu Asn Leu Pro Ala Leu Ala Gln Pro Arg Leu Glu Gly Leu Ser
                 85                  90                  95

Ala Gln Val Gly Glu Ser Cys Ser Met Ser Val Leu Asp Gly Thr Asp
            100                 105                 110

Ile His Tyr Val Ser Arg Val Ala Val Arg Lys Ile Met Thr Val Asn
            115                 120                 125

Ile Thr Ile Gly Thr Arg Phe Pro Ala His Ser Thr Ser Met Gly Arg
        130                 135                 140

Val Ile Leu Ser Gly Met Pro Asp Ala Asp Ile Arg Ser Phe Leu Asp
145                 150                 155                 160

Ser Val Pro Leu Glu His Gly Leu Thr Pro Arg Ser Leu Thr Asp Lys
                165                 170                 175

Glu Gln Leu Phe Ala Glu Ile Ile Ala Val Arg Asn Gln Gly Trp Ser
                180                 185                 190

Leu Val Asp Gln Glu Leu Glu Leu Gly Leu Arg Ser Leu Ala Ala Pro
            195                 200                 205

Ile Phe Asp Ala Asp Gly Lys Ile Val Ala Ala Ile Asn Ile Ser Thr
        210                 215                 220

Gln Ser Ala Val Ser Ser Val His Glu Leu Thr Ser Asn Tyr Leu Pro
225                 230                 235                 240

Val Leu Leu Ala Thr Ala Asp Glu Ile Ser Arg Asp Leu His Met Ala
                245                 250                 255

Ser Thr

<210> SEQ ID NO 28
<211> LENGTH: 24
<212> TYPE: DNA
<213> ORGANISM: Artificial Sequence
<220> FEATURE:
<223> OTHER INFORMATION: synthetic operator sequence from PcaR-
      responsive promoter

<400> SEQUENCE: 28
gtttgttcga taatcgcacg aacg                                          24

<210> SEQ ID NO 29
<211> LENGTH: 15
<212> TYPE: DNA
<213> ORGANISM: Artificial Sequence
<220> FEATURE:
<223> OTHER INFORMATION: synthetic operator sequence from PcaR-
      responsive promoter

<400> SEQUENCE: 29
gctcgcacat cgcac                                                    15

<210> SEQ ID NO 30
<211> LENGTH: 16
```

```
<212> TYPE: DNA
<213> ORGANISM: Artificial Sequence
<220> FEATURE:
<223> OTHER INFORMATION: synthetic operator sequence from PcaR-
      responsive promoter

<400> SEQUENCE: 30
agttcgataa tcgcac                                                      16

<210> SEQ ID NO 31
<211> LENGTH: 24
<212> TYPE: DNA
<213> ORGANISM: Artificial Sequence
<220> FEATURE:
<223> OTHER INFORMATION: synthetic operator sequence with point mutation
      from PcaR-responsive promoter

<400> SEQUENCE: 31
gtttgttcga taatcgcacg aacc                                             24

<210> SEQ ID NO 32
<211> LENGTH: 15
<212> TYPE: DNA
<213> ORGANISM: Artificial Sequence
<220> FEATURE:
<223> OTHER INFORMATION: synthetic operator sequence with point mutation
      from PcaR-responsive promoter

<400> SEQUENCE: 32
gctcgcagat cgcac                                                       15

<210> SEQ ID NO 33
<211> LENGTH: 14
<212> TYPE: DNA
<213> ORGANISM: Artificial Sequence
<220> FEATURE:
<223> OTHER INFORMATION: synthetic operator sequence from DcuR-
      responsive promoter

<400> SEQUENCE: 33
ttttaatttc aaaa                                                        14

<210> SEQ ID NO 34
<211> LENGTH: 14
<212> TYPE: DNA
<213> ORGANISM: Artificial Sequence
<220> FEATURE:
<223> OTHER INFORMATION: synthetic operator sequence from DcuR-
      responsive promoter

<400> SEQUENCE: 34
taattaacta ttat                                                        14

<210> SEQ ID NO 35
<211> LENGTH: 14
<212> TYPE: DNA
<213> ORGANISM: Artificial Sequence
<220> FEATURE:
<223> OTHER INFORMATION: synthetic operator sequence from DcuR-
      responsive promoter

<400> SEQUENCE: 35
tacaaaactt taaa                                                        14

<210> SEQ ID NO 36
<211> LENGTH: 14
<212> TYPE: DNA
<213> ORGANISM: Artificial Sequence
```

```
<220> FEATURE:
<223> OTHER INFORMATION: synthetic operator sequence from DcuR-
      responsive promoter

<400> SEQUENCE: 36
tagtaattaa atta                                                         14

<210> SEQ ID NO 37
<211> LENGTH: 23
<212> TYPE: DNA
<213> ORGANISM: Artificial Sequence
<220> FEATURE:
<223> OTHER INFORMATION: synthetic operator sequence from DctD-
      responsive promoter

<400> SEQUENCE: 37
actggtgcat cttttcggcc agg                                               23

<210> SEQ ID NO 38
<211> LENGTH: 18
<212> TYPE: DNA
<213> ORGANISM: Artificial Sequence
<220> FEATURE:
<223> OTHER INFORMATION: synthetic operator sequence from DctD-
      responsive promoter

<400> SEQUENCE: 38
tgtgcggaaa tccgcaca                                                     18

<210> SEQ ID NO 39
<211> LENGTH: 23
<212> TYPE: DNA
<213> ORGANISM: Artificial Sequence
<220> FEATURE:
<223> OTHER INFORMATION: synthetic DctD operator sequence from promoter
      pDctA

<400> SEQUENCE: 39
actggtgcat cttttcggcc agg                                               23

<210> SEQ ID NO 40
<211> LENGTH: 18
<212> TYPE: DNA
<213> ORGANISM: Artificial Sequence
<220> FEATURE:
<223> OTHER INFORMATION: synthetic DctD operator sequence from promoter
      pDctA

<400> SEQUENCE: 40
tgtgcggaaa tccgcaca                                                     18

<210> SEQ ID NO 41
<211> LENGTH: 60
<212> TYPE: DNA
<213> ORGANISM: Artificial Sequence
<220> FEATURE:
<223> OTHER INFORMATION: synthetic amplifcation primer P1 for E. coli
      dcuS gene

<400> SEQUENCE: 41
tttttggtag agaaagagga gaaatactag atgagacatt cattgcccta ccgcatgtta       60

<210> SEQ ID NO 42
<211> LENGTH: 60
<212> TYPE: DNA
<213> ORGANISM: Artificial Sequence
<220> FEATURE:
<223> OTHER INFORMATION: synthetic amplifcation primer P2 for E. coli
``` dcuS gene

<400> SEQUENCE: 42
tgatcatcta gtatttctcc tctttctcta tcatctgttc gacctctccc cgtcccaggg          60

<210> SEQ ID NO 43
<211> LENGTH: 60
<212> TYPE: DNA
<213> ORGANISM: Artificial Sequence
<220> FEATURE:
<223> OTHER INFORMATION: synthetic amplifcation primer P3 for E. coli
      dcuR gene

<400> SEQUENCE: 43
cagatgatag agaaagagga gaaatactag atgatcaatg tattaattat cgatgacgac          60

<210> SEQ ID NO 44
<211> LENGTH: 60
<212> TYPE: DNA
<213> ORGANISM: Artificial Sequence
<220> FEATURE:
<223> OTHER INFORMATION: synthetic amplifcation primer P4 for E. coli
      dcuR gene

<400> SEQUENCE: 44 agttttttgtt cgggcccaag cttcagatcc ttattggcaa tattgtttca gtagtgagta        60

<210> SEQ ID NO 45
<211> LENGTH: 60
<212> TYPE: DNA
<213> ORGANISM: Artificial Sequence
<220> FEATURE:
<223> OTHER INFORMATION: synthetic amplifcation primer P5 for E. coli
      pDcuB promoter

<400> SEQUENCE: 45
ttcgttttat ctgttgtttg tcggtgaact gtgtttttaa tttcaaaacg ctaacaaaag         60

<210> SEQ ID NO 46
<211> LENGTH: 60
<212> TYPE: DNA
<213> ORGANISM: Artificial Sequence
<220> FEATURE:
<223> OTHER INFORMATION: synthetic amplifcation primer P6 for E. coli
      pDcuB promoter

<400> SEQUENCE: 46
ccctccttat ctattctgcg taataaaata tatttaaatt tttgctgaat agatcacagt         60